(12) United States Patent
Burton et al.

(10) Patent No.: US 12,290,672 B2
(45) Date of Patent: May 6, 2025

(54) APPLICATOR FOR APPLYING A MICRONEEDLE DEVICE TO SKIN

(71) Applicant: KINDEVA DRUG DELIVERY L.P., St. Paul, MN (US)

(72) Inventors: Scott A. Burton, Woodbury, MN (US); Craig S. Moeckly, White Bear Lake, MN (US); Ryan P. Simmers, Fargo, ND (US)

(73) Assignee: Kindeva Drug Deliver L.P., Woodbury, MN (US)

( * ) Notice: Subject to any disclaimer, the term of this patent is extended or adjusted under 35 U.S.C. 154(b) by 1211 days.

(21) Appl. No.: 17/066,867

(22) Filed: Oct. 9, 2020

(65) Prior Publication Data

US 2021/0030975 A1 Feb. 4, 2021

Related U.S. Application Data

(62) Division of application No. 14/759,757, filed as application No. PCT/US2014/010447 on Jan. 7, 2014, now abandoned.

(Continued)

(51) Int. Cl.
*A61M 5/50* (2006.01)
*A61M 37/00* (2006.01)

(52) U.S. Cl.
CPC ...... *A61M 5/5086* (2013.01); *A61M 37/0015* (2013.01); *A61M 2037/0023* (2013.01);
(Continued)

(58) Field of Classification Search
CPC ............ A61M 5/5086; A61M 5/31545; A61M 5/31546; A61M 5/31548; A61M 5/31533;
(Continued)

(56) References Cited

U.S. PATENT DOCUMENTS 5,359,993 A * 11/1994 Slater .................... G06M 1/041
606/205
5,364,001 A * 11/1994 Bryan .............. A61B 17/07207
227/19

(Continued)

FOREIGN PATENT DOCUMENTS

CN 102497909 6/2012
EP 1834589 9/2007

(Continued)

OTHER PUBLICATIONS

Extended European Search Report for EP 21173161.7 issued by the European Patent Office on Dec. 2, 2021; 8 pgs.

(Continued)

*Primary Examiner* — Joel M Attey
*Assistant Examiner* — Alexandra Lalonde
(74) *Attorney, Agent, or Firm* — Mueting Raasch Group

(57) ABSTRACT

Various embodiments of an applicator and a method for applying a microneedle device to skin are disclosed. The applicator can include a housing and a reciprocating support structure slidably engaged with the housing. The reciprocating support structure can have a plurality of alignment feet. The applicator can have a lockout mechanism that prevents actuation if any of the plurality of the alignment feet are not evenly aligned. The applicator can include a device life indicator that is capable of counting a number of use cycles that the applicator has undergone and providing feedback to a user. The applicator can include a dose timer capable of determining a time that has elapsed after the actuation of the applicator and providing feedback to the user.

21 Claims, 13 Drawing Sheets

Related U.S. Application Data

(60) Provisional application No. 61/750,128, filed on Jan. 8, 2013.

(52) U.S. Cl.
CPC .............. *A61M 2037/0046* (2013.01); *A61M 2205/106* (2013.01)

(58) Field of Classification Search
CPC .......... A61M 5/31536; A61M 5/31541; A61M 5/14248; A61M 37/0015; A61M 2037/0023; A61M 2037/0061; A61M 2037/0046; A61M 2037/003; A61M 2205/106; A61M 2205/581; A61M 2205/583; A61M 2205/332; A61M 2005/3125; A61M 2005/3126; A61M 2005/3154; A61M 2005/3254; A61M 2005/3267; A61M 2005/14252; A61M 2005/208; A61M 2005/2073; A61M 5/31535; A61M 5/31501; A61M 5/31538; A61M 5/31566; A61M 5/31568; A61M 5/31571; A61M 5/158; A61M 5/315; A61M 5/31565; A61M 5/31576; A61M 5/32; A61M 5/3287; A61M 5/3295; A61M 5/3298; A61M 5/50; A61M 2037/0053; A61M 2205/33; A61M 2205/35; A61M 2205/353; A61M 2205/50; A61M 2205/502; A61M 2205/52; A61M 2205/58; A61M 2205/82; A61M 2205/8206; A61M 2005/31508; A61M 2005/1585; A61M 2005/1588; A61M 2210/04; A61B 2017/00115; A61B 2090/0803

See application file for complete search history.

(56) References Cited

U.S. PATENT DOCUMENTS

| | | | |
|---|---|---|---|
| 6,091,975 A | 7/2000 | Daddona | |
| 6,293,925 B1 | 9/2001 | Safabash | |
| 6,312,612 B1 | 11/2001 | Sherman | |
| 6,379,324 B1 | 4/2002 | Gartstein | |
| 6,537,242 B1* | 3/2003 | Palmer | A61M 37/0015 600/583 |
| 6,558,361 B1 | 5/2003 | Yeshurun | |
| 6,855,131 B2 | 2/2005 | Trautman | |
| 7,080,642 B2 | 7/2006 | Hodson | |
| 7,097,631 B2 | 8/2006 | Trautman | |
| 7,131,960 B2 | 11/2006 | Trautman | |
| 7,648,484 B2 | 1/2010 | Yeshurun | |
| 2002/0087182 A1 | 7/2002 | Trautman | |
| 2002/0123675 A1* | 9/2002 | Trautman | A61B 5/150984 606/183 |
| 2002/0156414 A1 | 10/2002 | Redding | |
| 2003/0050602 A1 | 3/2003 | Pettis | |
| 2004/0049150 A1 | 3/2004 | Dalton | |
| 2005/0096586 A1 | 5/2005 | Trautman | |
| 2005/0165358 A1* | 7/2005 | Yeshurun | A61M 37/0015 604/173 |
| 2005/0261631 A1 | 11/2005 | Clarke | |
| 2006/0229570 A1 | 10/2006 | Lovell | |
| 2007/0106207 A1 | 5/2007 | Withey | |
| 2008/0039805 A1 | 2/2008 | Frederickson | |
| 2008/0208146 A1 | 8/2008 | Brandwein | |
| 2009/0198189 A1 | 8/2009 | Simons | |
| 2010/0222743 A1 | 9/2010 | Frederickson | |
| 2010/0256568 A1 | 10/2010 | Frederickson | |
| 2011/0105951 A1* | 5/2011 | Bernstein | A61B 5/150297 600/573 |
| 2011/0213335 A1 | 9/2011 | Burton | |
| 2011/0218383 A1 | 9/2011 | Broen | |
| 2012/0103328 A1 | 5/2012 | Smith | |
| 2012/0109066 A1 | 5/2012 | Chase | |
| 2012/0123387 A1 | 5/2012 | Gonzalez | |
| 2012/0130207 A1 | 5/2012 | O'dea | |
| 2012/0143119 A1* | 6/2012 | Deasey | A61M 37/0015 604/20 |
| 2012/0184906 A1 | 7/2012 | McAllister | |
| 2013/0053752 A1* | 2/2013 | Xu | A61K 9/06 604/173 |
| 2013/0131602 A1 | 5/2013 | Kemp | |
| 2015/0352295 A1 | 12/2015 | Burton | |

FOREIGN PATENT DOCUMENTS

| | | |
|---|---|---|
| EP | 2236083 | 10/2010 |
| EP | 2460553 | 6/2012 |
| KR | 10-2008-0040568 A | 5/2008 |
| WO | WO 2006-037434 | 4/2006 |
| WO | WO 2010-033770 | 3/2010 |
| WO | 20110115602 | 9/2011 |
| WO | WO 2011-140240 | 11/2011 |
| WO | WO 2012-030316 | 3/2012 |
| WO | WO 2012-074576 | 6/2012 |
| WO | 2010098339 | 9/2012 |
| WO | WO 2012-122162 | 9/2012 |
| WO | WO 2014-110016 | 7/2014 |

OTHER PUBLICATIONS

International Search report for PCT International Application No. PCT/US2014/010447 mailed on Mar. 21, 2014, 3 pages.

Supplemental European Search report for European Application No. EP 14 73 7512 dated Sep. 5, 2016, 2 pages.

\* cited by examiner

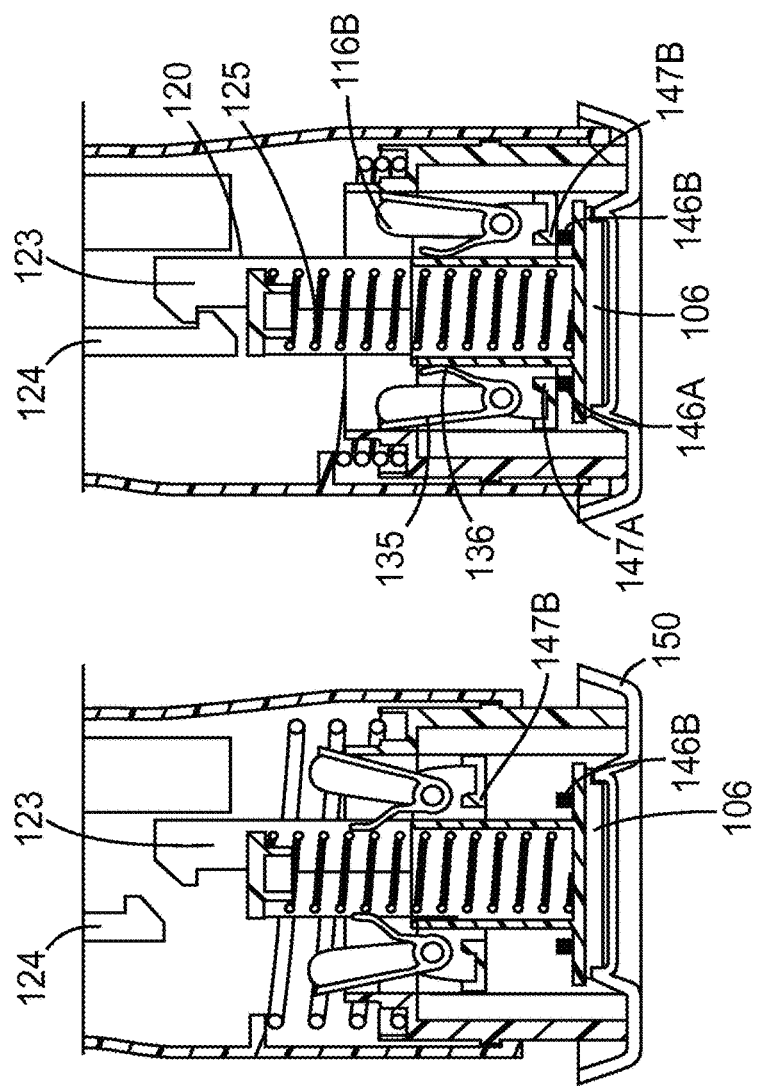
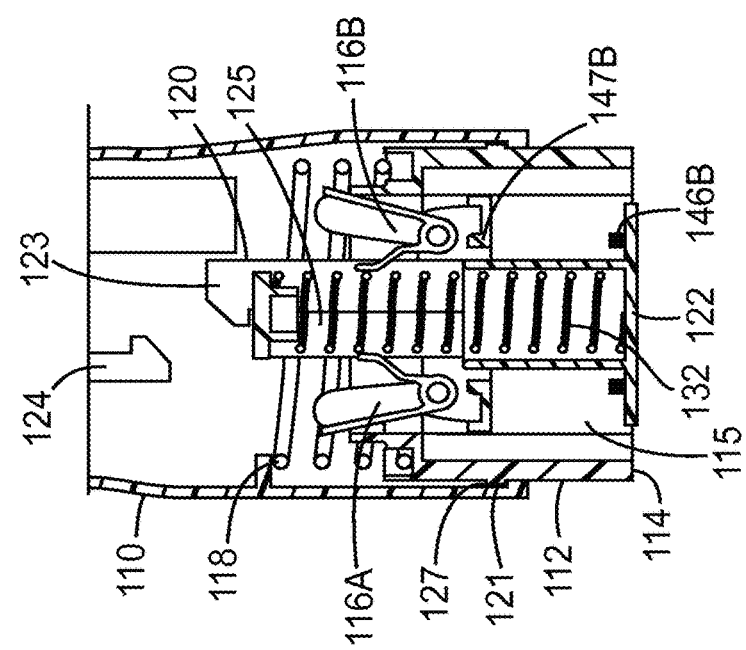

APPLICATOR FOR APPLYING A MICRONEEDLE DEVICE TO SKIN

CROSS REFERENCE TO RELATED APPLICATIONS

This application is a divisional application of U.S. patent application Ser. No. 14/759,757, filed Jul. 8, 2015, now abandoned, which is a national stage filing under 35 U.S.C. 371 of PCT/US2014/010447, filed Jan. 7, 2014, which claims priority to U.S. Provisional Patent Application No. 61/750,128, filed Jan. 8, 2013, the disclosures of which are incorporated by reference in their entireties herein.

FIELD

The present disclosure generally relates to applicators and methods for applying a microneedle device to skin to treat an area of the skin and/or to deliver an active agent to the skin.

BACKGROUND

Transdermal and topical drug delivery can be used for therapeutic treatment, but the number of molecules that can be effectively delivered using these routes can be limited by the barrier properties of skin. The main barrier to transport of molecules through the skin is the stratum corneum (the outermost layer of the skin).

A number of different skin treatment methods have been proposed in order to increase the permeability or porosity of the outermost skin layers, such as the stratum corneum, thus enhancing drug delivery through or into those layers. The stratum corneum is a complex structure of compact keratinized cell remnants separated by lipid domains. The stratum corneum is formed of keratinocytes, which comprise the majority of epidermal cells, that lose their nuclei and become corneocytes. These dead cells comprise the stratum corneum, which has a thickness of only about 10-30 microns and protects the body from invasion by exogenous substances and the outward migration of endogenous fluids and dissolved molecules. Various skin treatment methods include the use of microneedles, laser ablation, RF ablation, heat ablation, sonophoresis, iontophoresis, or a combination thereof.

Devices including arrays of relatively small structures, sometimes referred to as microneedles or micro-pins, have been disclosed for use in connection with the delivery of therapeutic agents and other substances through the skin and other surfaces. The devices are typically pressed against the skin in an effort to pierce the stratum corneum such that the therapeutic agents and other substances can sequentially or simultaneously pass through that layer and into the tissues below. Microneedles of these devices pierce the stratum corneum upon contact, making a plurality of microscopic slits which serve as passageways through which molecules of active components can be delivered into the body. In delivering an active component, the microneedle device can be provided with a reservoir for temporarily retaining an active component in liquid form prior to delivering the active component through the stratum corneum. In some constructions, the microneedles can be hollow to provide a liquid flow path directly from the reservoir and through the microneedles to enable delivery of the therapeutic substance through the skin. In alternate constructions, active component(s) may be coated on the microneedle array and delivered directly through the skin after the stratum corneum has been punctured.

Microneedle arrays and patches can be deployed with an applicator device capable of being used a number of different times. The microneedle arrays and patches are generally used once and then discarded. The applicator devices can be repeatedly reloaded with new microneedle arrays and patches. The present invention provides an alternative microneedle array applicator device.

SUMMARY

The present disclosure relates to applicators that can be used to treat a selected site (e.g., on skin), and/or to apply an active ingredient to the treated site.

One aspect of the present disclosure provides an applicator for applying a microneedle device. The applicator can include a housing having a first open end configured so as to accept the microneedle device and a second end configured as a graspable handle. The applicator can further include a driving element contained within the housing, the driving element having a first end configured so as to couple with the microneedle device and an actuation button in mechanical or electrical engagement with the driving element. The applicator can further include at least one reciprocating support structure slidably engaged with the housing, wherein the reciprocating support structure has a first position where at least a portion of it extends from the first open end of the housing by a first distance and a second position wherein the portion extends from the first open end of the housing by a second distance, the second distance being less than the first distance.

Another aspect of the present disclosure provides an applicator for applying a microneedle device where the applicator can include a housing having a first open end configured so as to accept the microneedle device and a second end configured as a graspable handle. The applicator can further include a driving element contained within the housing, the driving element having a first end configured so as to couple with the microneedle device and an actuation button in mechanical or electrical engagement with the driving element. The applicator can further include a device life indicator in mechanical or electrical engagement with at least one of the driving element or the actuation button, wherein the device life indicator is capable of counting the number of use cycles that the applicator has undergone and, based on the number of use cycles, providing feedback to the user as to the use status of the applicator.

Another aspect of the present disclosure provides an applicator for applying a microneedle device where the applicator can include a housing having a first open end configured so as to accept the microneedle device and a second end configured as a graspable handle. The applicator can further include a driving element contained within the housing, the driving element having a first end configured so as to couple with the microneedle device and an actuation button in mechanical or electrical engagement with the driving element. The applicator can further include a dose timer in mechanical or electrical engagement with at least one of the driving element or the actuation button, wherein the dose timer is capable of determining the time that has elapsed after actuation of the device and providing feedback to the user as to the time that the microneedle device has been in place on the skin surface.

Other features and aspects of the present disclosure will become apparent by consideration of the detailed description and accompanying drawings.

BRIEF DESCRIPTION OF THE DRAWINGS

FIG. 2A is a side partial cross sectional view of the lower, skin-contacting portion of an applicator according to one embodiment of the present disclosure.

FIG. 2B is a side partial cross sectional view of the lower, skin-contacting portion of an applicator according to one embodiment of the present disclosure, where the applicator is in contact with a microneedle device in a priming fixture.

FIG. 2C is a side partial cross sectional view of the lower, skin-contacting portion of an applicator according to one embodiment of the present disclosure, where the applicator is in contact with a microneedle device in a priming fixture.

DETAILED DESCRIPTION

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the term "coupled" and variations thereof are used broadly and encompass both direct and indirect couplings. Furthermore, terms such as "front," "rear," "top," "bottom," "upward," "downward," "under," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

The present disclosure generally relates to an applicator and method for applying a microneedle device, comprising an array of microneedles, to skin (or a biological membrane) to treat the skin (i.e., create small holes or perforations or micropores in the skin) and/or to deliver an active agent to the skin.

Figure 1A:
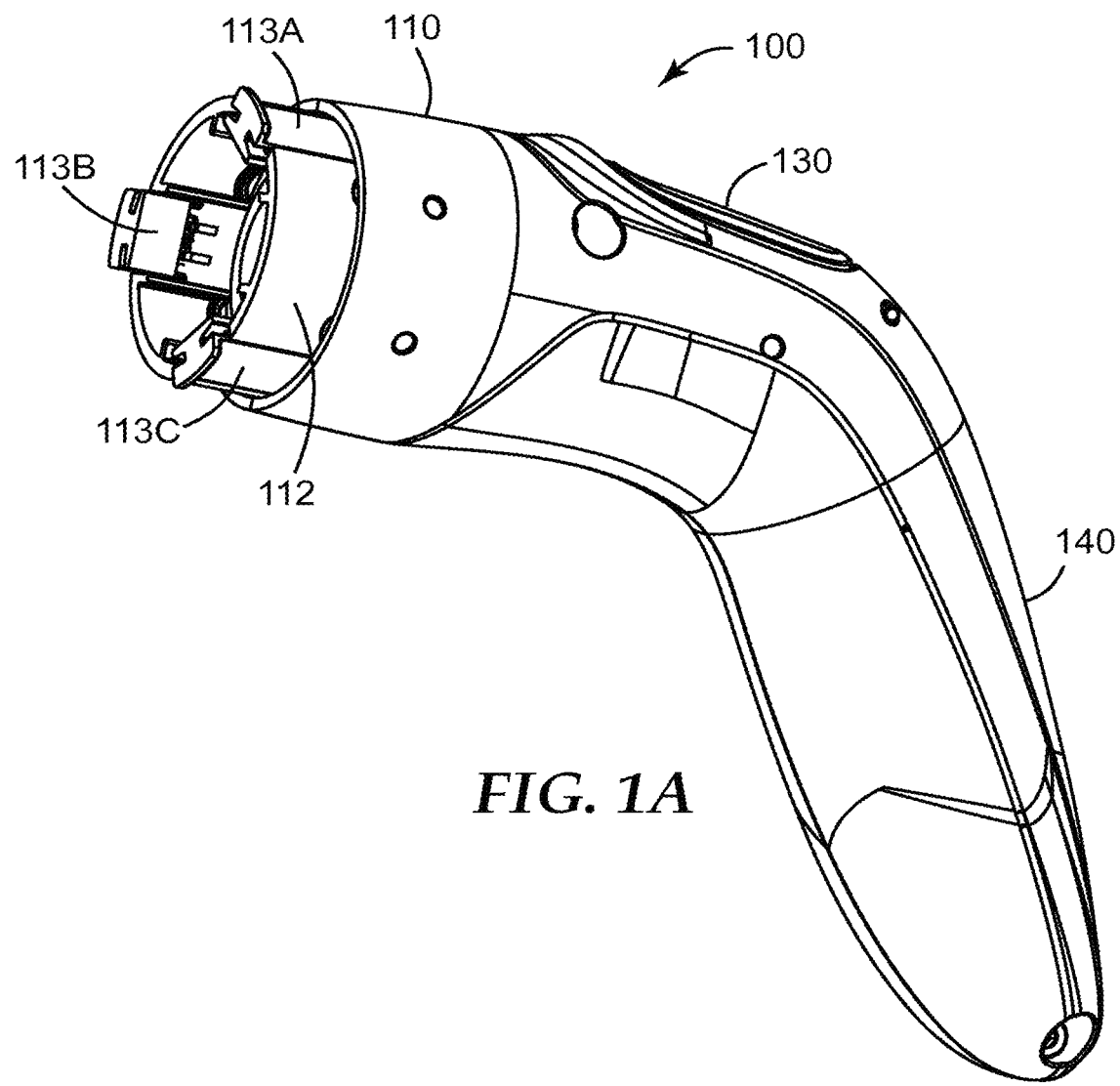
FIG. 1A is a perspective view of an applicator according to one embodiment of the present disclosure.
Figure 1B:
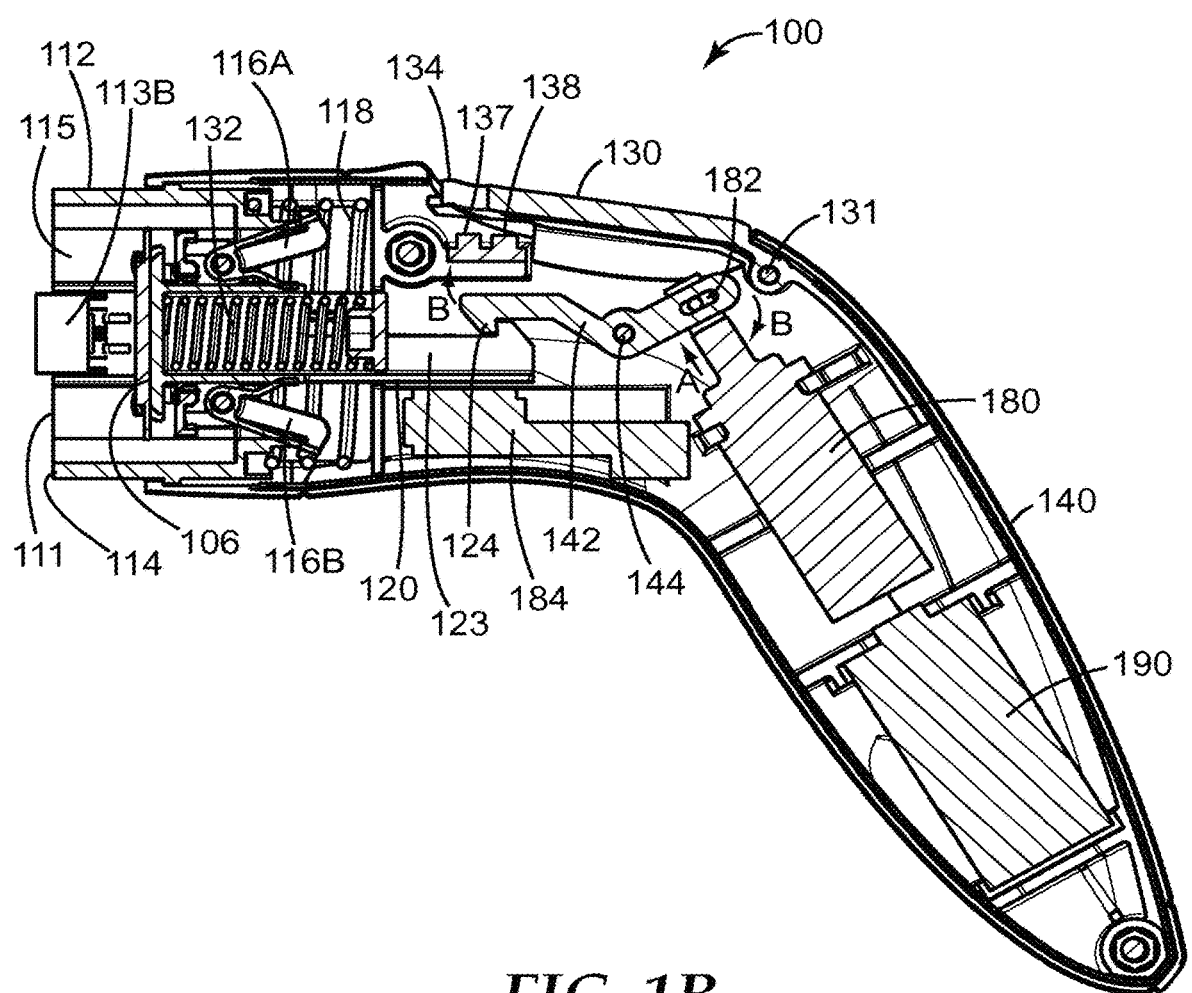
FIG. 1B is a side cross sectional view of an applicator according to one embodiment of the present disclosure.
Figure 2F:
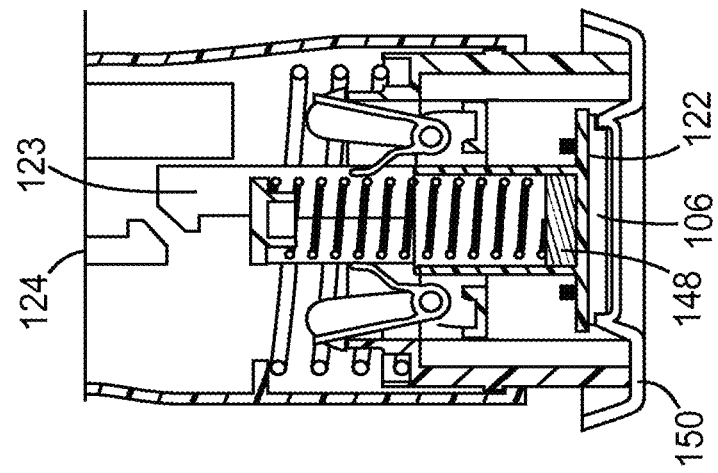
FIG. 2F is a side partial cross sectional view of the lower, skin-contacting portion of an applicator according to one embodiment of the present disclosure, where the applicator employs magnetic attachment means.

In one embodiment, as shown in FIGS. 1-2, an applicator 100 has a lower housing 110 and an upper housing or handle 140. The lower housing 110 has an internal cavity 115 with an opening 111 at its lower end. The upper end of the lower housing 110 connects to the handle 140. The lower housing 110 is configured to accommodate a driving element 120, such as a piston; a reciprocating support structure, such as a reciprocating collar 112; a piston latch 124, reciprocating collar spring 118; and rocker arms 116A,B. Alignment feet 113A,B,C, are in sliding engagement with the reciprocating collar 112.

The opening 111 and internal cavity 115 are sized so as to allow a microneedle device 106 to be placed inside of the internal cavity. As described in more detail below, the microneedle device 106 will include a microneedle array and may also include other structures or components, such as a backing film and/or adhesive. The reciprocating collar 112 is movable between a first, extended position (as shown in FIGS. 2A and 2D) and a second, retracted position (as shown in FIG. 2C). When the reciprocating collar 112 is in the first, extended position, the collar spring 118 urges the collar 112 to its outermost position. The collar 112 is retained within the lower housing 110 by the interaction of collar stop 127 and mechanical stop 121 on the inside of the lower housing 110 which prevents the collar 112 from being ejected from the housing.

As shown in FIG. 2A, the applicator 100 is in a first configuration where the piston 120 extends out of the lower housing 110 and just beyond the outer, optionally skin-contacting, edge 114 of the reciprocating collar 112. The piston 120 is urged outward by driving spring 132 while being retained within the lower housing 110 by the interaction between piston hook 123 and the top of the piston track 125. In this first configuration the applicator 100 can be brought into contact with a priming fixture 150 upon which a microneedle device 106 is supported. The priming fixture 150 is configured such that the microneedles 108 of the microneedle device 106 face downward, that is, away from the piston face 122, but are protected from damage. This may be accomplished by having the microneedle device 106 rest on contact surfaces of the priming fixture 150 that contact a portion of the microneedle device 106 that is free of microneedles 108, thus allowing the microneedles 108 to be suspended in one or more cavities formed in the priming fixture 150.

Figure 3B:
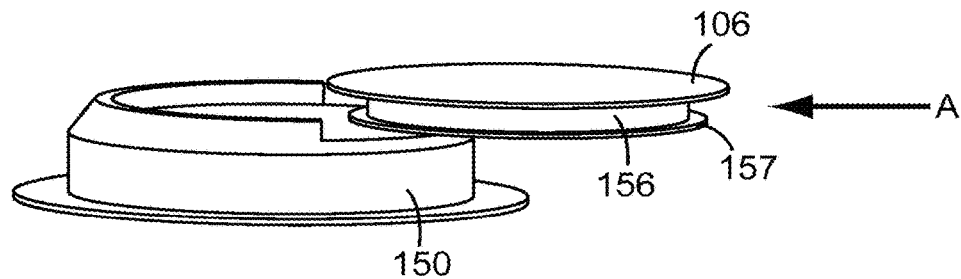
FIG. 3B is a perspective view of microneedle device and a priming fixture according to one embodiment of the present disclosure.
Figure 3A:
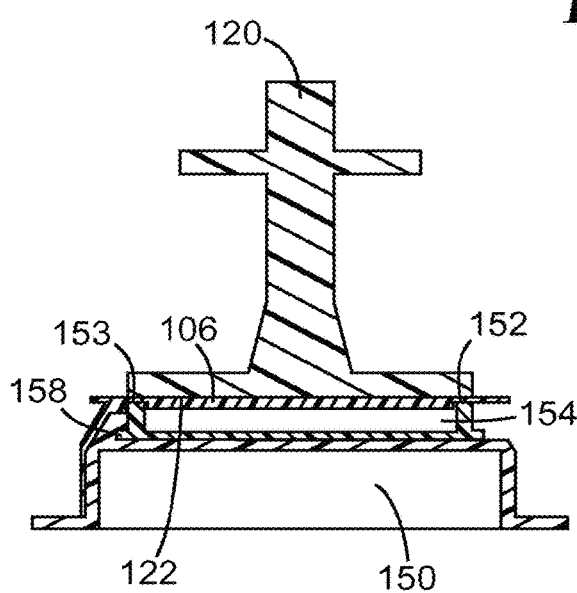
FIG. 3A is a side partial cross sectional view of an applicator in contact with a priming fixture according to one embodiment of the present disclosure.
Figure 3C:
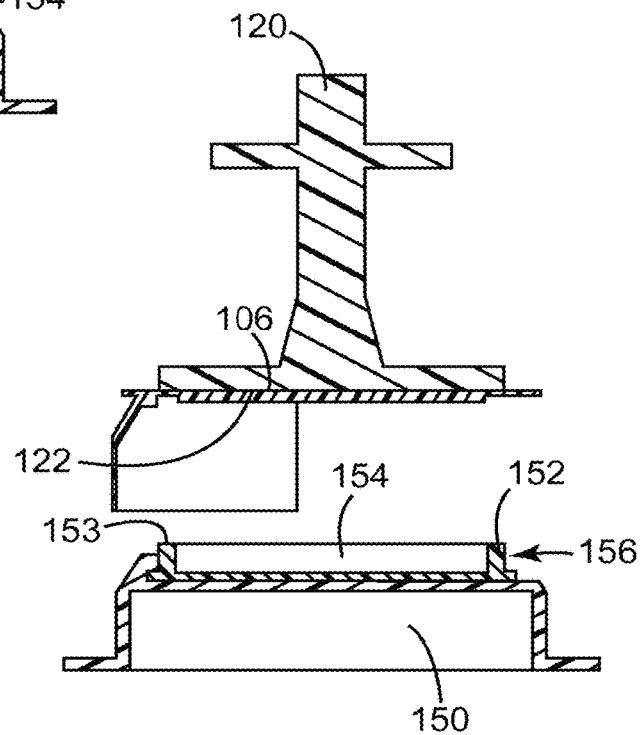
FIG. 3C is a side partial cross sectional view of an applicator and a priming fixture according to one embodiment of the present disclosure.

In one embodiment, the microneedle device 106 may be provided to a user with a protective cover 156 that protects the microneedle device 106 and in particular the microneedles 108 during storage (see FIGS. 3B-C). The cover 156 has protective contact surfaces 152, 153 that support the microneedle device 106 and allow the microneedles 108 to be suspended in cavity 154. The cover 156 is sized and shaped so that it may slide in the direction of arrow A onto the priming fixture 150. The cover 156 has an extending lip 157 that mates with a slot 158 in the priming fixture 150. After the applicator 100 has coupled with the microneedle device 106 (as shown in FIG. 3A) and been lifted away from the priming fixture (as shown in FIG. 3C), the protective cover 156 remains coupled to the priming fixture 150. In one embodiment, the protective cover 156 may then be subsequently removed from the priming fixture 150 so that the priming fixture 150 may be reused with another microneedle device 106. Examples of suitable protective covers are described in more detail in U.S. Patent Application Publication No. US 2010/0256568 A1 (Frederickson et al.), the disclosure of which is incorporated herein by reference.

In one embodiment, the microneedle device 106 may be provided to a user already mounted on the priming fixture 150, in which instance the priming fixture 150 also serves as a protective cover for the microneedle device 106 during storage.

Figure 12A:
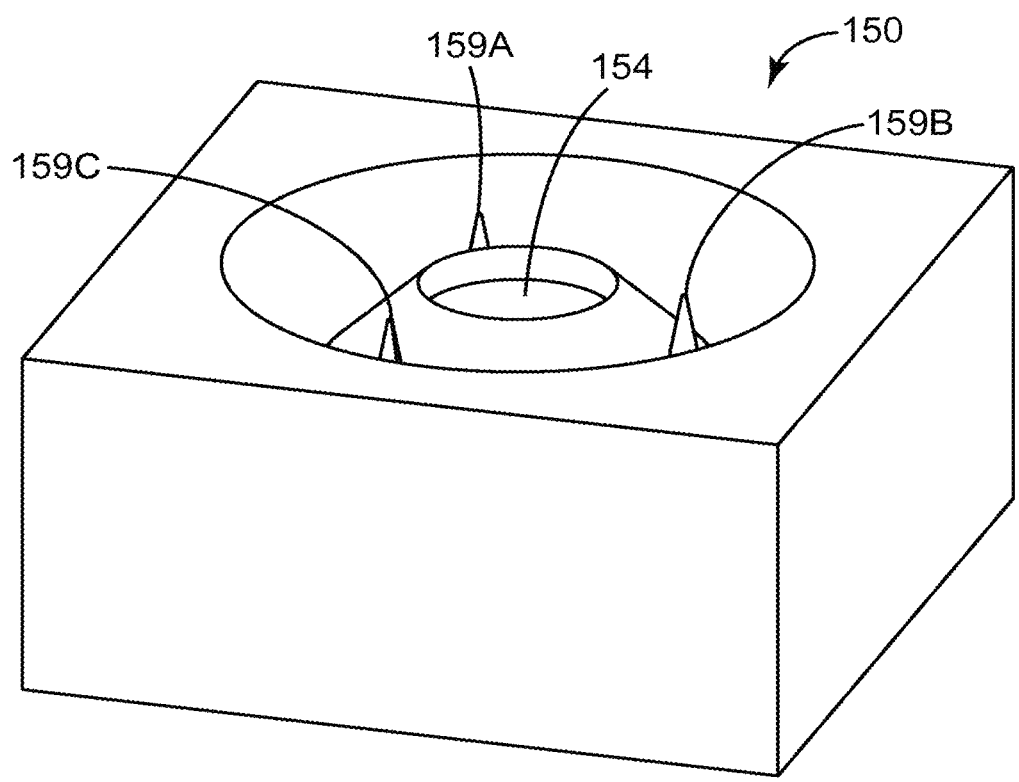
FIG. 12A is perspective view of a priming a priming fixture according to one embodiment of the present disclosure.
Figure 12B:
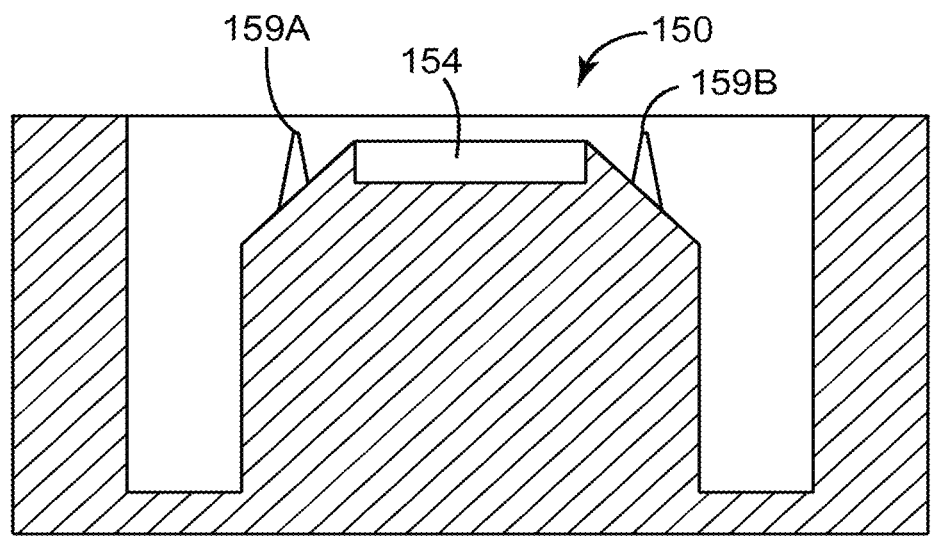
FIG. 12B is a side cross-sectional view of a priming fixture according to one embodiment of the present disclosure.

In one embodiment, the portion of the priming fixture 150 that contacts the microneedle device 106 may comprise narrow pins 159A,B,C that extend above the cavity 154 as shown in FIGS. 12A, B. Minimizing the area of contact between priming fixture 150 and microneedle device 106 is particularly advantageous when the surface of the microneedle device 106 facing the priming fixture 150 has an exposed pressure sensitive adhesive. Minimization of the contact area allows for the microneedle device to be easily removed from the priming fixture 150 when it is temporarily affixed to the applicator 100 (as described in greater detail below).

Although described with relation to a priming fixture 150, the applicator 100 of the present invention may by coupled to the microneedle device 106 and primed by other methods. For example, a user could manually grasp the microneedle device 106 and attach it to the piston face 122 or the applicator 100 could come preloaded with a microneedle device 106 during initial manufacture. Likewise, the piston 120 could be primed by manually pressing on a portion of the microneedle device 106, preferably a portion of the microneedle device 106 without protruding microneedles, in order to compress the driving spring 132 and lock it into its primed position as described below.

In use, a user will grasp the applicator 100 by the upper housing (or handle) 140 and bring the applicator 100 into contact with the priming fixture 150 so that the outer edge 114 of the reciprocating collar 112 contacts the base of the priming fixture 150 and the piston 120 is partially retracted into the internal cavity 115 of the lower housing 110. The driving spring 132 will be partially compressed, thereby causing the piston to press with a predetermined force against the microneedle device 106 (that depends on the spring strength and the height of the priming fixture) that assists in temporarily attaching the microneedle device 106 to the piston face 122. Various methods of attachment may be used, including, but not limited to, press-fit or friction-fit engagement, snap-fit engagement, magnets, hook-and-loop fasteners, and adhesives, or combinations thereof.

In one embodiment a relatively weak adhesive is used, such that the microneedle device 106 is bonded sufficiently to the piston face 122 to allow it to be retracted into the applicator 100, but after the applicator 100 is activated and the microneedle device 106 attaches to a skin surface (as described in further detail below), the bond between microneedle device 106 and skin is greater than the bond between microneedle device 106 and piston face 122, thus allowing the microneedle device to be easily detached from the piston face 122.

In one embodiment, a small permanent magnet 148 (shown in FIG. 2F) is placed inside the piston 120 and just above the piston face 122. The microneedle device 106 may have a thin metallic foil placed in or on the upper surface of the microneedle device, thus allowing it to be temporarily attached to the piston face 122.

Following alignment with the priming fixture 150 and temporary attachment of the microneedle device 106 to the piston face 122, the applicator 100 is pressed further downwards. The resulting compression of the collar spring 118 allows the reciprocating collar 112 to slide into the housing 110 (as shown in FIG. 2C) into a second, retracted position. In this position, the rocker arms 116A,B are compressed between the collar 112 and the piston 120 with a first rocker arm extension member 135 pressed up against the interior of the collar 112 and a second rocker arm extension member 136 pressed up against the exterior of the piston 120. In this configuration, the rocker arms 116A,B do not impede motion of either collar 112 or piston 120. The microneedle device 106 is also temporarily coupled to the piston face 122. The piston hook 123 slides over the piston catch 124. Piston contacts 146A,B are brought into contact with housing contacts 147A,B which sends a signal to logic board 184 to indicate that the piston 120 is fully retracted. The logic board 184 sends a signal to the solenoid 180 causing the upper end 182 of the solenoid 180 to push in the direction of the arrow A thereby causing the piston catch 124 to mate with the piston hook 123 and thus holding the piston 120 in its fully retracted state where the driving spring 132 is fully compressed. The applicator 100 may further provide an optional user feedback signal to inform the user that the piston 120 has been latched to the housing and that the driving spring 132 is fully compressed.

Although attachment of the microneedle device 106 to the piston face 122 and priming are described as sequential steps above, in principle they could occur simultaneously. That is, the force between microneedle device 106 and piston face 122 would only become sufficient to achieve temporary attachment when the driving spring 132 was fully compressed in its primed position. In practice, however, it is preferable that the force necessary to achieve this temporary attachment is less than the force needed to fully compress and prime the driving spring 132, so as to ensure attachment of the microneedle device 106 to the piston face 122.

As the applicator 100 is lifted from the priming fixture 150 the collar spring 118 expands back towards its initial state (as shown in FIG. 2D). As the collar 112 moves downward in the lower housing 110 the rocker arms 116A,B and in particular the rocker arm latches 117A,B are biased away from the piston 120 and the rocker arm latches 117A,B hook onto the upper edge of the collar 112. The microneedle device 106, now coupled to the piston face 122, is retracted into the internal cavity 115 of the lower housing 110.

The collar 112 is retained within the lower housing 110 by the interaction of collar stop 127 and mechanical stop 121 on the inside of the lower housing 110 which prevents the collar 112 from being ejected from the housing.

It will be readily appreciated that the ability of the collar 112 to slide into the housing 110 into a second, retracted position allows for use of a relatively low-profile priming fixture 150, while still allowing the piston face 122 to contact and couple to the microneedle device 106 held in the priming fixture. Use of a low-profile priming fixture 150 may be advantageous as it can allow for more compact packaging and even offer the possibility of packaging each microneedle device 106 with its own priming fixture 150, rather than using a reusable priming fixture.

As shown in FIG. 2D, the applicator 100 is loaded and primed and ready to be applied to a patient. In this configuration the piston 120 is coupled to the piston catch 124 via the piston hook 123. The collar 112 is fixed in its extended position, since it is prevented from moving up into the housing 110 by its interaction with the rocker arm latches 117A,B and it is prevented from moving further outward from the housing 110 by its interaction with mechanical stop 121. Thus the collar 112 acts as if it is rigidly attached to the housing 110. Also shown in FIG. 2D is alignment foot 113B which is biased to partially extend from the internal cavity 115 formed by the collar 112. Alignment foot 113B is one of 3 alignment feet 113A,B,C in this embodiment.

In order to deploy the microneedle device 106, the user will move the outer edge 114 of the collar 112 towards a skin surface 170. In doing this the alignment feet 113A,B,C will first come into contact with the skin surface 170 and retract into the internal cavity 115 formed by the collar 112 as the user presses the applicator 100 closer to the skin surface 170. Each alignment foot 113A,B,C has an electrical contact 133 which can contact a complementary contact in the applicator housing and thus send a signal to the logic board 184 when the alignment foot is sufficiently retracted. If one or more of the alignment feet is not sufficiently retracted (and thus not sending a signal to the logic board 184), then the applicator 100 will be prevented from applying the patch by disabling the piston release mechanism (described in further detail below). The requirement for retraction of all three alignment feet 113A,B,C minimizes the chance that the applicator 100 could be inadvertently activated before it is brought into contact with the skin surface of a patient. In addition, the requirement for retraction of all three alignment feet 113A, B,C helps to ensure that the applicator 100 is held firmly against the skin surface 170 and held generally perpendicular to the skin surface 170 prior to applying the microneedle device 106 to the skin surface 170.

Figure 2E:
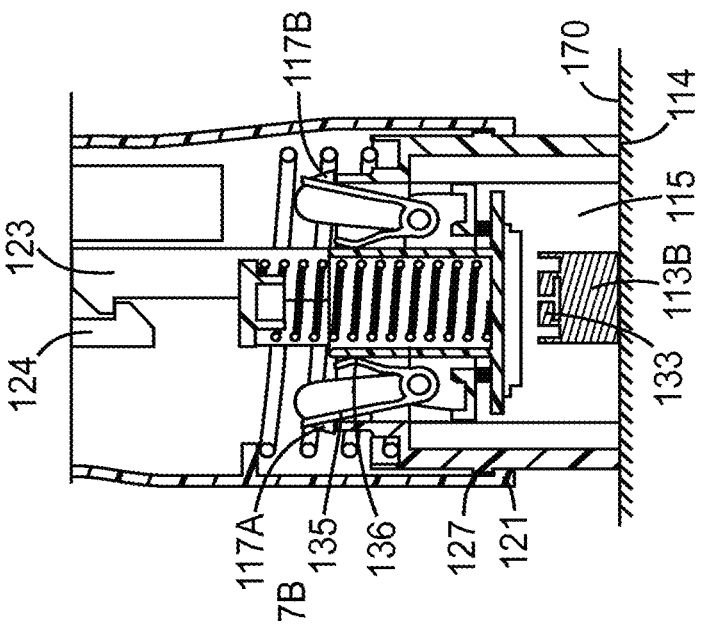
FIG. 2E is a side partial cross sectional view of the lower, skin-contacting portion of an applicator according to one embodiment of the present disclosure, where the applicator is in contact with a skin surface, but prior to actuation.
Figure 2D:
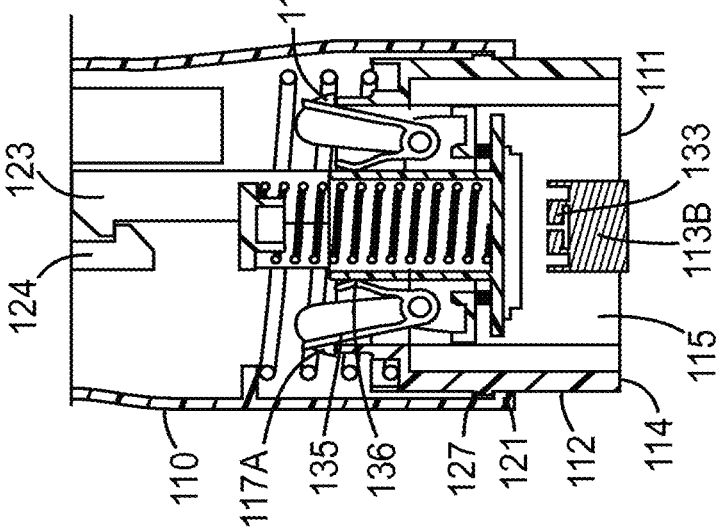
FIG. 2D is a side partial cross sectional view of the lower, skin-contacting portion of an applicator according to one embodiment of the present disclosure, where the applicator has been primed.

In one embodiment, as shown in FIG. 2E, it is desired that the alignment feet 113A,B,C must be fully retracted into the housing before allowing for activation. This allows the outer edge 114 of the applicator 100 to contact the skin surface 170 before or essentially simultaneously with the signals sent to the logic board 184 which allow for activation of the applicator 100.

In one embodiment, a visual indicator 137, visible through an indicator window 134, would light up, green for instance, to indicate to the user that the alignment feet are all retracted and that the device is ready to be actuated. Alternatively, the visual indicator could change color, from red to green for instance, to indicate to the user that the alignment feet are all retracted and that the device is ready to be actuated.

The user actuates the applicator 100 by pressing on the actuator button 130, which causes the actuator button 130 to rotate about the actuator button pivot 131. The actuator button 130 rotates into contact with the actuator contact 138 which causes a signal to be sent to the logic board to indicate that the actuator button 130 has been depressed. When the logic board simultaneously receives the signals indicating that the alignment feet 113A,B,C are properly retracted and the actuator button 130 is depressed, then it sends a signal to solenoid 180 causing the upper end 182 of the solenoid 180 to rotate the piston release lever 142 about the piston release lever pivot 144 in the direction as shown by arrows B. This rotational movement causes piston catch 124 to disengage from the piston hook 123, thus allowing the piston 120 to be biased out of the housing 110 by the driving spring 132 and thereby applying the microneedle device 106 to the skin surface. The user then lifts the applicator 100 away from the skin surface 170 and the applicator 100 will be in its "free" state as shown in FIG. 2A.

In one embodiment, the microneedle device 106 will have a skin-facing adhesive that causes the microneedle device 106 to adhere to the skin surface 170 with a force greater than the connection force between the microneedle device 106 and the piston face 122. Thus the microneedle device 106 will detach from the piston face 122 when the user lifts the applicator 100 away from the skin surface 170, thereby allowing the microneedle device 106 to remain for an extended period of time on the skin surface 170. In an alternative embodiment, the microneedle device 106 will remain attached to the piston face 122 when the user lifts the applicator 100 away from the skin surface 170 and the microneedle device 106 can subsequently be manually removed from the piston face 122 and disposed of by the user prior to reusing the applicator 100.

Power to the logic board 184, visual indicator 137, solenoid 180, and any other electrical components of the device is provided by battery 190.

Figure 4:
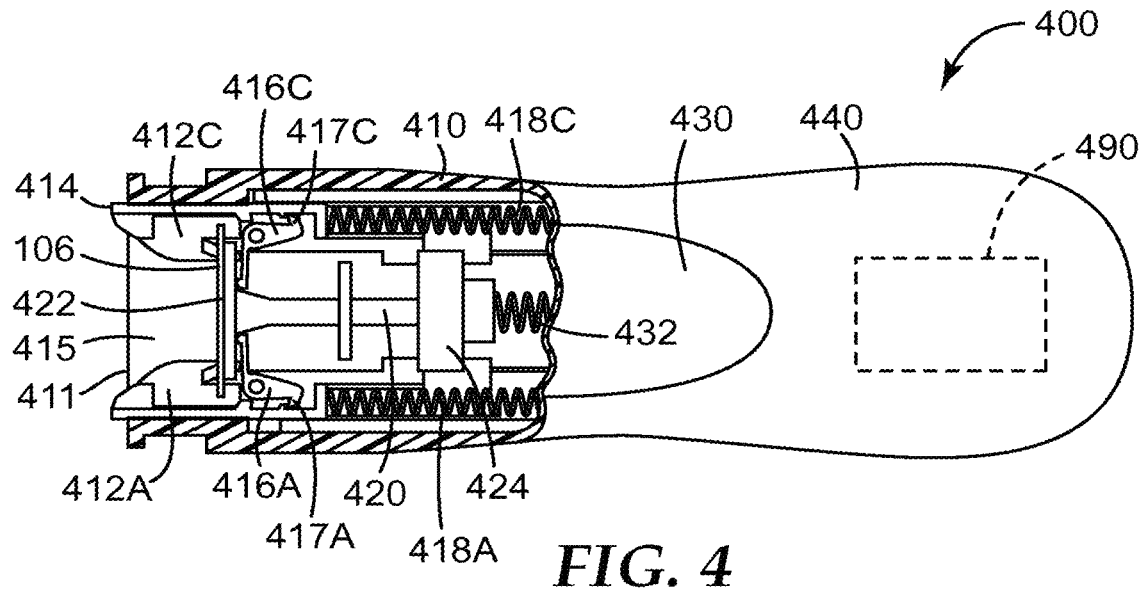
FIG. 4 is a top partial cross sectional view of an applicator according to one embodiment of the present disclosure.
Figure 5:
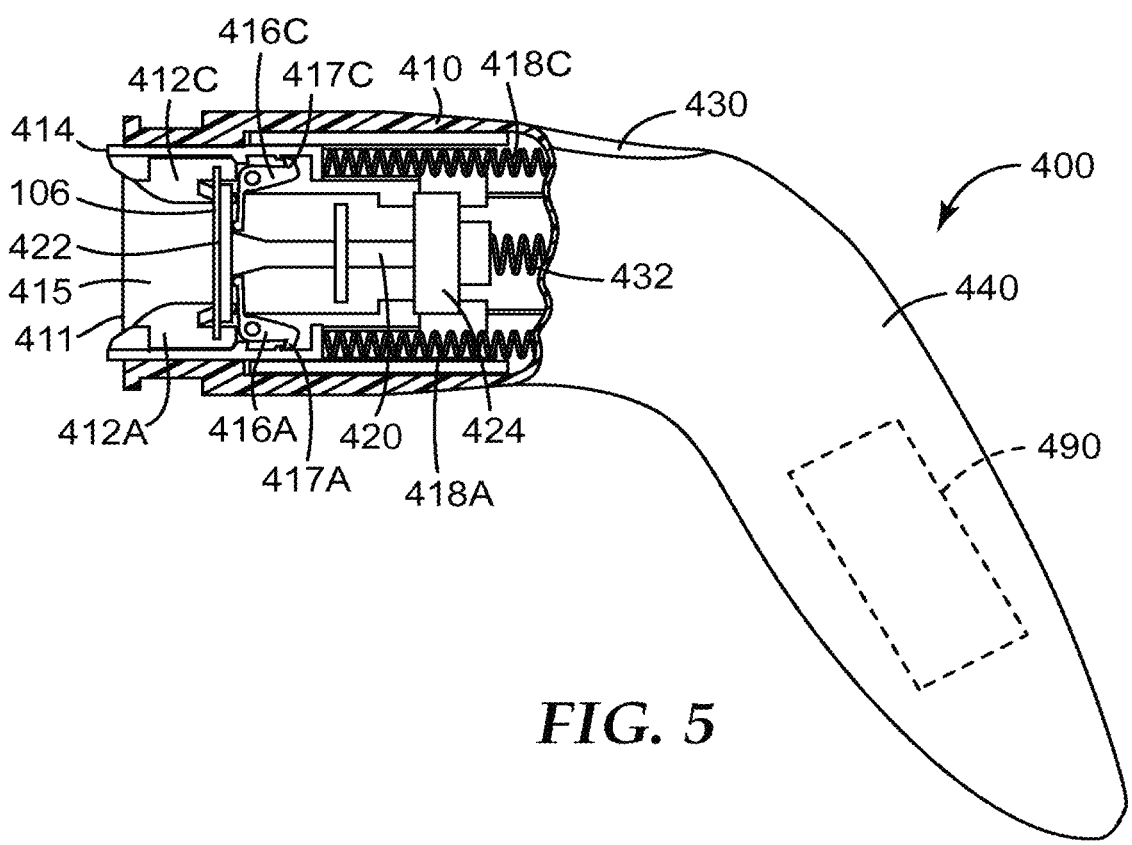
FIG. 5 is a side partial cross sectional view of an applicator according to one embodiment of the present disclosure.

In another embodiment, as shown in FIGS. 4-6, an applicator 400 has a lower housing 410 and an upper housing or handle 440. The lower housing 410 has an internal cavity 415 with an opening 411 at its lower end. The upper end of the lower housing 410 connects to the handle 440. The lower housing 410 is configured to accommodate a driving element 420, such as a piston; reciprocating support structures 412A,B,C,D; a piston latch 424, reciprocating support structure springs 418A,B,C,D; and rocker arms 416A,B,C,D. The reciprocating support structures 412A,B,C,D are also referred to below as alignment arms. Likewise, the reciprocating support structure springs 418A,B,C,D are also referred to below as alignment arm springs.

It should be understood that FIGS. 4-6 show a variety of cross-sectional or partial cut-away views of the applicator 400 and as such only one or two alignment arms 412A,B,C,D and only one or two alignment arm springs 418A,B,C,D, etc. are shown in FIGS. 4-6, but the applicator 400 described in FIGS. 4-6 has 4 alignment arms and 4 alignment arm springs, some of which are not shown in the various partial views.

Figure 6A:
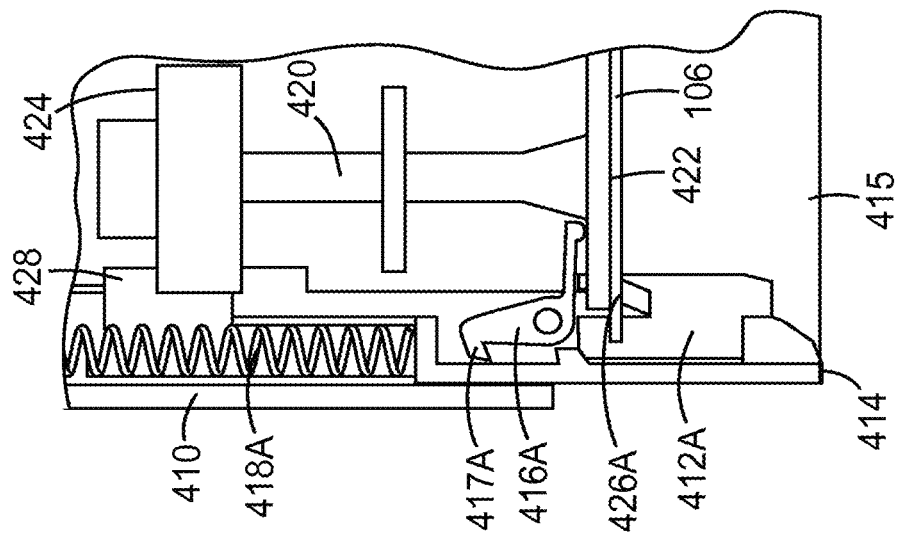
FIG. 6A is a side partial cross sectional view of the lower, skin-contacting portion of an applicator according to one embodiment of the present disclosure, where the applicator is in contact with a microneedle device in a priming fixture.
Figure 6B:
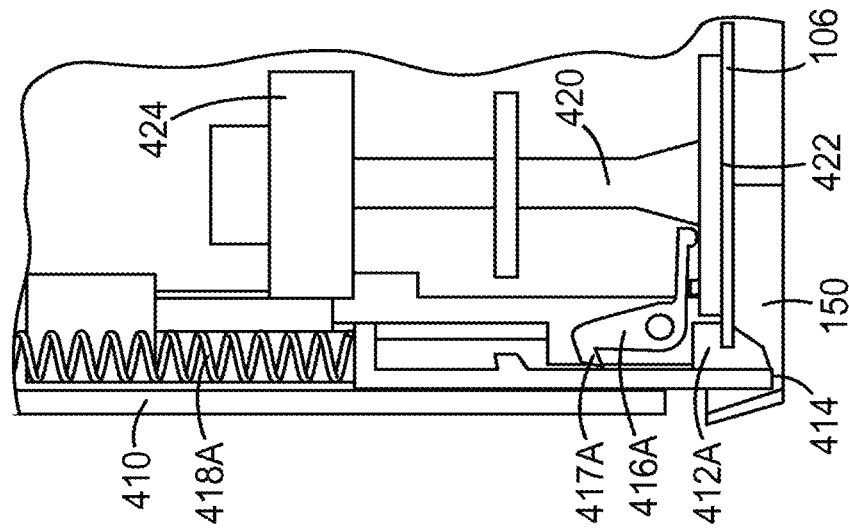
FIG. 6B is a side partial cross sectional view of the lower, skin-contacting portion of an applicator according to one embodiment of the present disclosure, where the applicator has been primed.
Figure 6C:
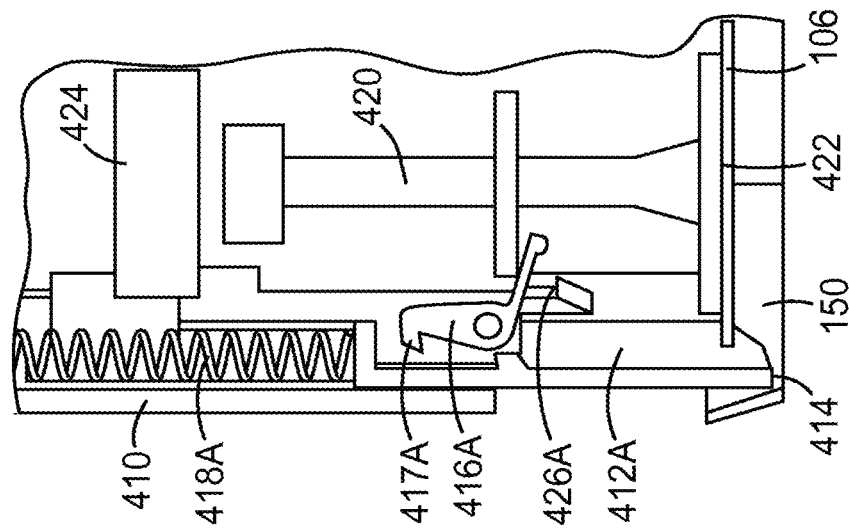
FIG. 6C is a side partial cross sectional view of the lower, skin-contacting portion of an applicator according to one embodiment of the present disclosure, where the applicator has been lifted away from a priming fixture.

The opening 411 and internal cavity 415 are sized so as to allow a microneedle device 106 to be placed inside of the internal cavity. The reciprocating alignment arms 412A,B,C,D are movable between a first, extended position (as shown in FIGS. 6A and 6C) and a second, retracted position (as shown in FIG. 6B). When the reciprocating alignment arms 412A,B,C,D are in the first, extended position, the alignment arm springs 418A,B,C,D urge the alignment arms 412A,B,C,D to their outermost position. The alignment arms 412A,B,C,D are retained within the lower housing 410 by a mechanical stop (not shown) on the inside of the lower housing 410 that prevents the alignment arms 412A,B,C,D from being ejected from the housing. As shown in FIG. 6A, the applicator 400 is in a first configuration where the piston 420 extends out of the lower housing 410, but does not extend as far as the alignment arms 412A,B,C,D. The piston 420 is urged outward by driving spring 432 while being partially retained within the lower housing 410 by the extension of rocker arm 416A. In this first configuration the applicator 400 can be brought into contact with a priming fixture 150 upon which a microneedle device 106 is resting. The priming fixture 150 is configured such that the microneedles 108 of the microneedle device 106 face downwards, that is, away from the piston face 422, but are protected from damage. This may typically be accomplished by having the microneedle device 106 rest on contact surfaces 152, 153 of the priming fixture 150 that contact a portion of the microneedle device 106 that is free of microneedles 108, thus allowing the microneedles 108 to be suspended in one or more cavities 154 formed in the priming fixture 150 (sec FIG. 3A).

In one embodiment, the microneedle device 106 may be provided to a user with a protective cover 156 that protects the microneedle device 106 and in particular the microneedles 108 during storage (see FIGS. 3B-C). The cover 156 is sized and shaped so that it may slide in the direction of arrow A onto the priming fixture 150. The cover 156 has an extending lip 157 that mates with a slot 158 in the priming fixture 150. After the applicator 400 has coupled with the microneedle device 106 (as shown in FIG. 3A) and been lifted away from the priming fixture (as shown in FIG. 3C), the protective cover 156 remains coupled to the priming fixture 150. In one embodiment, the protective cover 156 may then be subsequently removed from the priming fixture 150 so that the priming fixture 150 may be reused with another microneedle device 106. Examples of suitable protective covers are described in more detail in U.S. Patent Application Publication No. US 2010/0256568 A1 (Frederickson et al.), the disclosure of which is incorporated herein by reference.

In one embodiment, the microneedle device 106 may be provided to a user already mounted on the priming fixture 150, in which instance the priming fixture 150 also serves as a protective cover for the microneedle device 106 during storage.

Following alignment with the priming fixture 150, the applicator 400 is pressed downwards, that is, towards the priming fixture 150 thus achieving several results. The resulting compression of the alignment arm springs 418A,B,C,D allows the alignment arms 412A,B,C,D to slide into the housing 410 (as shown in FIG. 6B) into a second, retracted position and further allow the piston face 422 and microneedle device 106 to slide past the housing latches 426A,B,C,D. The top of the piston 420 mates with the piston catch 424 and temporarily locks the two parts together. The rocker arms 416A,B,C,D rotate up so that the rocker arm latches 417A,B,C,D rest against the alignment arms 412A,B,C,D. As shown, the microneedle device 106 is temporarily held against the piston face 422 by the housing latches 426A,B,C,D. Various alternative methods of attachment may be used, including, but not limited to, press-fit or friction-fit engagement, snap-fit engagement, magnets, hook-and-loop fasteners, and adhesives, or combinations thereof.

As the applicator 400 is lifted from the priming fixture 150 the alignment arm springs 418A,B,C,D expand back towards their initial state (as shown in FIG. 6C). The microneedle device 106, now coupled to the piston face 422, is retracted into the internal cavity 415 of the lower housing 410. The applicator 400 is loaded and primed and ready to be applied to a patient. In this configuration the piston 420 is coupled to the piston catch 424 and the piston catch 424 is prevented from rotating due to its interaction with the piston catch stop 428. The actuation button 430 is mechanically coupled to the piston catch 424 (connecting mechanism not shown) so as to be able to rotate the piston catch 424 when the actuation button 430 is depressed. Since the piston catch 424 is prevented from rotating in this configuration, then the actuation button 430 is locked in place and cannot be depressed by the user, thus preventing the applicator 400 from being inadvertently activated before it is brought into contact with the skin surface of a patient.

Upon removal of the applicator 400 away from the priming fixture 150 the alignment arms 412A,B,C,D extend back to their first position, thus allowing for the microneedle device 106 to be recessed further within the applicator 400 away from the skin-contacting surface 414. It will be readily appreciated, however, that the ability of the alignment arms 412A,B,C,D to slide into the housing 410 into a second, retracted position allows for use of a relatively low-profile priming fixture 150, while still allowing the piston face 422 to contact and couple to the microneedle device 106 held in the priming fixture. Use of a low-profile priming fixture 150 may be advantageous as it can allow for more compact packaging and even offer the possibility of packaging each microneedle device 106 with its own priming fixture 150, rather than using a reusable priming fixture.

Figure 6E:
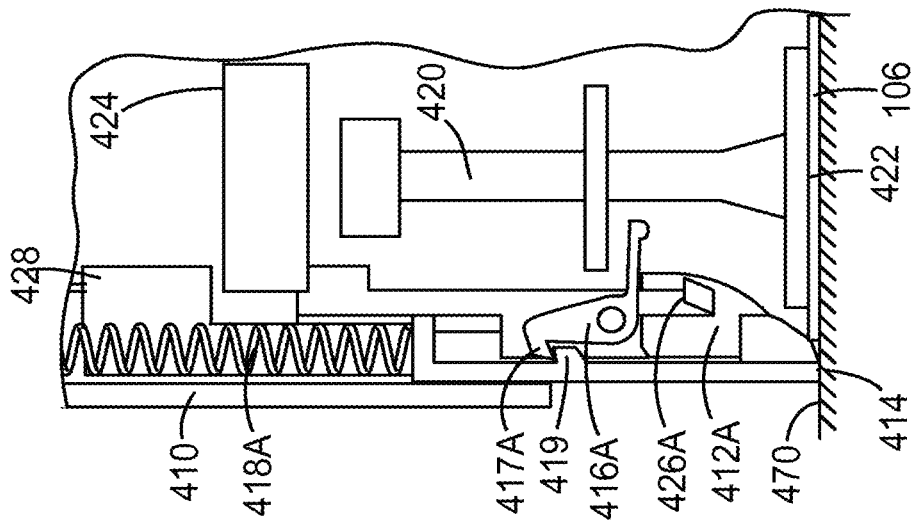
FIG. 6E is a side partial cross sectional view of the lower, skin-contacting portion of an applicator according to one embodiment of the present disclosure, where the applicator has been actuated.
Figure 6D:
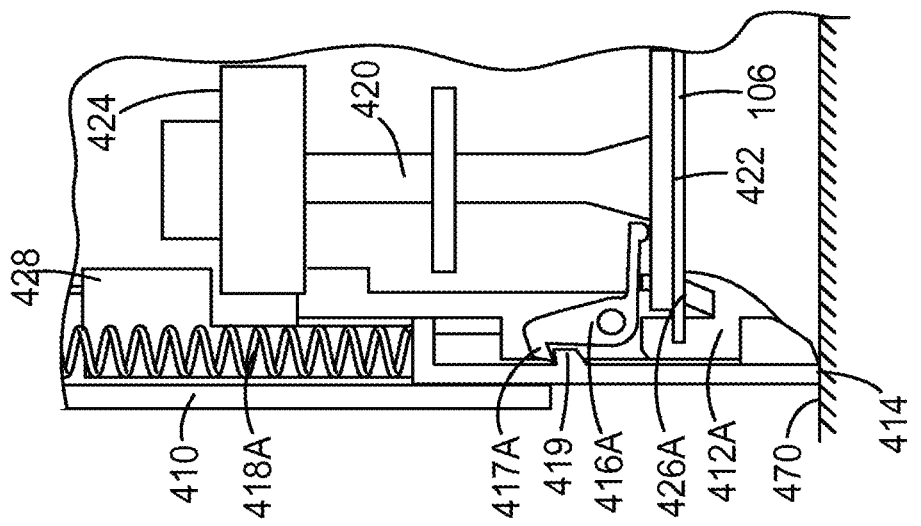
FIG. 6D is a side partial cross sectional view of the lower, skin-contacting portion of an applicator according to one embodiment of the present disclosure, where the applicator is in contact with a skin surface, but prior to actuation.

In use, the skin-contacting surface 414 of the applicator 400 is brought into contact with a skin surface 470 and the applicator 400 is pressed downwards as shown in FIG. 6D. The alignment arm springs 418A,B,C,D are partially compressed, thus partially retracting the reciprocating alignment arms 412A,B,C,D into the lower housing 410. The alignment arms 412A,B,C,D cannot be completely retracted into the housing 410, however, since the rocker arm latches 417A,B,C,D are caught by the alignment arm latch 419, thus preventing further retraction of the alignment arms 412A,B,C,D. In this configuration the piston catch 424 has moved downwards and no longer is engaged with the piston catch stop 428. The device may then be actuated by pressing down on the actuation button 430 which causes the piston catch 424 to rotate, thus releasing the piston 420 which is driven against the skin surface 470 by the expansion of a driving spring (not shown) to attach the microneedle device 106 to the skin surface 470 (as shown in FIG. 6E). The force of the driving spring is sufficient to push the microneedle device 106, which preferably has flexible outer edges past the housing latches 426A,B,C,D which temporarily retained the microneedle device within the housing of the applicator 400. In a preferred embodiment, the applicator 400 is then detached from the microneedle device 106 leaving the microneedle device 106 in place on the skin surface 470. Because the alignment arms 412A,B,C,D can be independently compressed, the above described mechanism will only release the piston catch 424 if all of the alignment arms 412A,B,C,D are equally retracted into the housing 410, thus ensuring that the applicator 400 and microneedle device 106 are aligned perpendicular to the skin surface 470 prior to actuating the applicator 400.

In one embodiment, the applicator 400 has a battery 490 that may be used to power various electrical or electromechanical functions as described elsewhere in the specification.

Although described in detail above for a device with 4 alignment arms and 4 alignment arm springs, it should be understood that the number of alignment arms (or reciprocating support structures) may vary as desired. In one embodiment, the applicator 400 has a single reciprocating support structure that preferably has a skin contacting surface in the form of a ring. In one embodiment, the applicator 400 has a plurality of support structures, which may also be referred to as alignment arms. It is a particular advantage of the device that when it contains two or more alignment arms, those alignment arms can be employed to ensure that the device is properly oriented with respect to the skin surface prior to actuation. In one embodiment the applicator 400 has more than two alignment arms and preferably 3 or 4 alignment arms. In one embodiment the applicator 400 has less than 10 alignment arms and preferably less than 5 alignment arms. In one embodiment each alignment arm will be coupled to an individual alignment arm spring.

Figure 9:
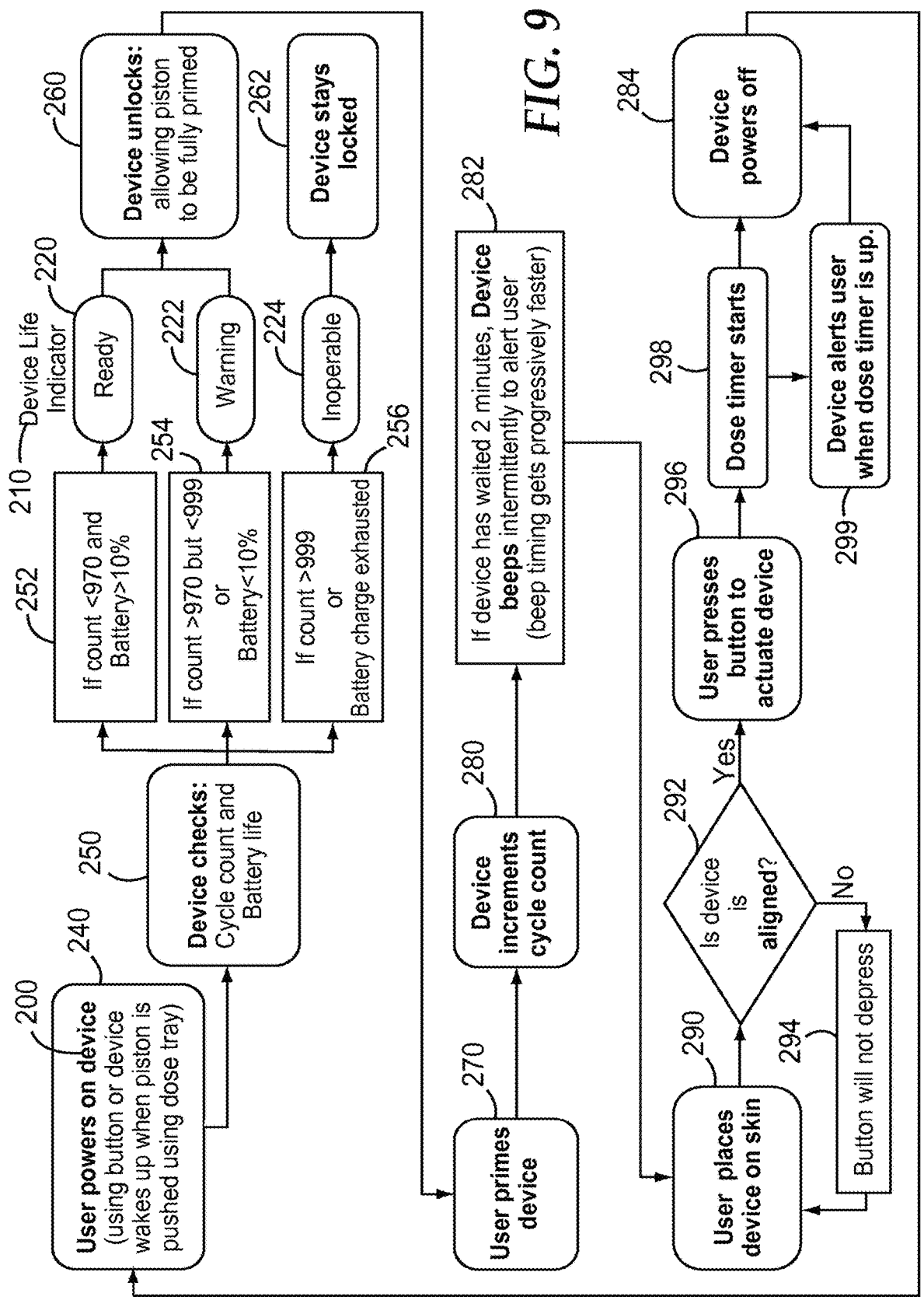
FIG. 9 is schematic flow-chart of the process by which a device life indicator functions for an applicator according to one embodiment of the present disclosure.

In one embodiment, the applicator or device 200 has a device life indicator 210. As shown in a process flow diagram in FIG. 9, in a first step 240 a user would power on the device 200, the device 200 would then perform an internal step 250 to check the cycle count, that is, the number of times the device 200 had been previously used. The device 200 could also optionally check the battery life of the device during step 250. If the cycle count and battery life meet predetermined acceptance criteria, then the device life indicator 210 would indicate that the device was "READY" 220 and the device 200 will undergo an internal step 260 of unlocking the device 200 so that it may be fully primed for use. For example, this may be accomplished by having the driving element or piston locked in place until the device undergoes the device check 250. The acceptance criteria will depend upon the robustness of the device 200 and the battery. For example, as shown in FIG. 9, for a device intended to be used for 1000 cycles and considered to function satisfactorily if the battery has more than 10% of its original charge, the device will indicate "READY" 220 if the device check 252 shows that the cycle count is less than 970 and the battery charge is greater than 10%. If the device check 254 shows that the count is between 970 and 999 and/or the battery is less than 10%, but still functioning, then the device life indicator 210 will indicate "WARNING" 222 to let the user know that the device is near the end of its usable life. If the device check 256 shows that the count is greater than 999 and/or the battery charge is exhausted, then the device life indicator 210 will indicate "INOPERABLE" 224 and the device 200 will remain locked 262 such that it can't be used further.

As described above, the device life indicator 210 provides feedback of "READY", "WARNING", or "INOPERABLE" 220, 222, 224. It should be understood that this feedback may take many other forms. For example, green, yellow, and red lights, may be used to indicate READY", "WARNING", or "INOPERABLE" 220, 222, 224 respectively.

Figure 10C:
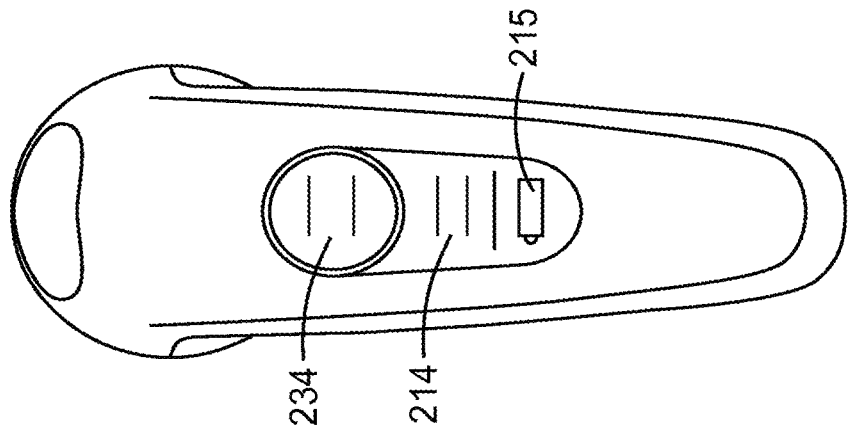
FIG. 10A-F are side elevation views of device life indicators and dose timer countdown features according to various embodiments of the present disclosure.
Figure 10B:
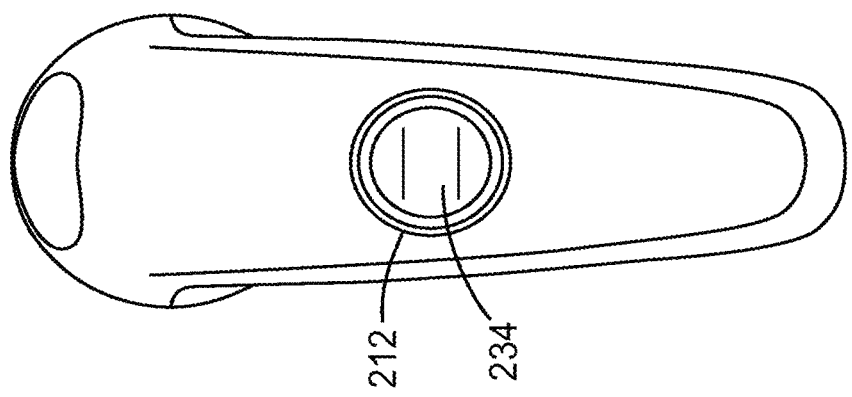
Figure 10A:
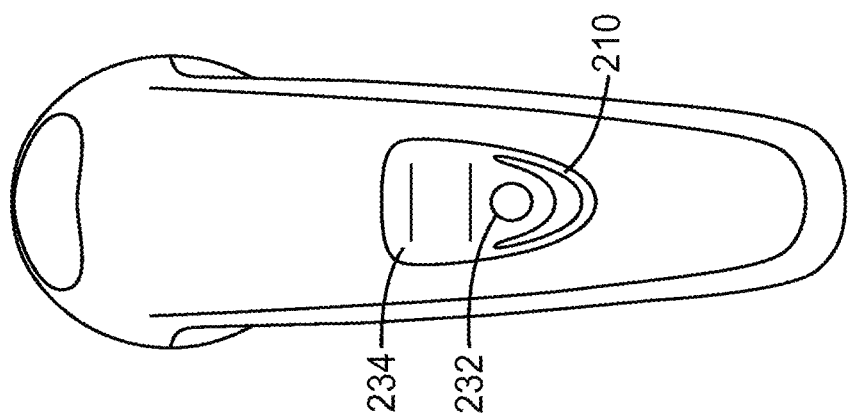

In one embodiment, as shown in FIG. 10A, the device life indicator 210 may take the form of a curved or U-shaped, "thermometer" type display. The device would initially show a full, green display to indicate that it had not been used. Over time the green color would "drain" from the display to indicate that the device was partially used. As the device approached end of life the color of the device life indicator could optionally change to yellow and finally red. Optionally, an indicator, such as an arrow, line, or bar, could move through zones colored green, yellow, and red to indicate the device status. It should be understood that any other suitable colored graphic display that changes color as the device approaches end of life or that changes the amount of color displayed as the device approaches end of life may be used as a device life indicator. Additionally, a separate device life warning could illuminate to provide additional feedback to indicate that the device was either near to end of life or at end of life.

In one embodiment, as shown in FIG. 10B, the device life indicator 212 may take the form of a circular, "thermometer" type display.

In one embodiment, as shown in FIG. 10C, the device life indicator 214 may take the form of a digital read-out indicating the percentage of useful life remaining.

In one embodiment, as shown in FIG. 10C, the device may include an optional battery gauge 215 to indicate the amount of usable battery life remaining.

Figure 10F:
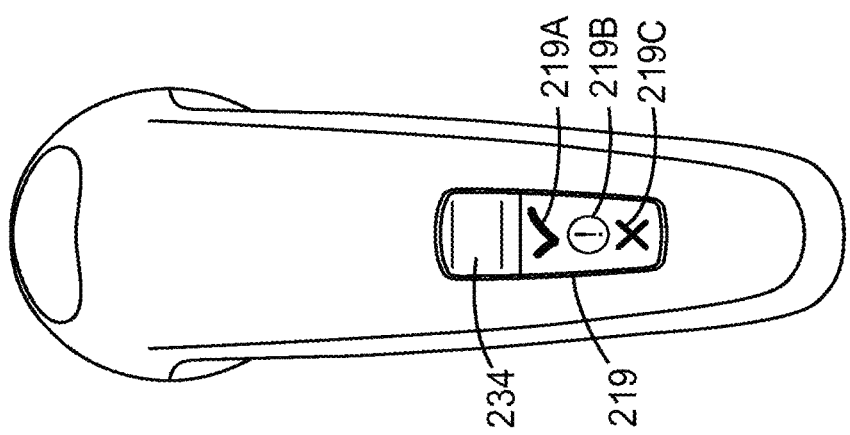
Figure 10E:
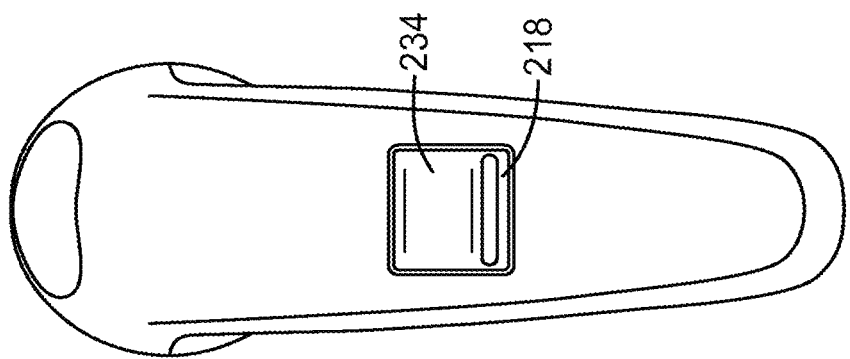
Figure 10D:
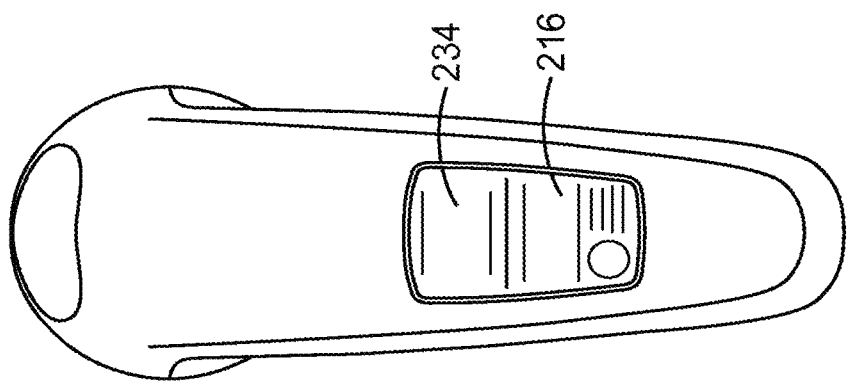

In one embodiment, as shown in FIG. 10D, the device life indicator 216 may take the form of a digital read-out 216 indicating the number of remaining cycles or uses that the device may be used for.

In one embodiment, as shown in FIG. 10E, the device life indicator 218 may take the form of a linear "thermometer" type display.

In one embodiment, as shown in FIG. 10F, the device life indicator 219 may take the form individual icons with, for example, a check mark 219A indicating that the device is ready to use, an exclamation point 219B indicating a warning that the device is nearly at the end of life, and an 'X' 219C indicating that the device is at end of life and is inoperable.

In one embodiment, as shown in FIGS. 10A-F, an additional dose timer 234 countdown feature can optionally be included on the device 200. This timer 234 indicates a time, generally in minutes or seconds, that a user is to leave a microneedle device 106 in place upon the skin after application. As the device 200 is actuated to apply the microneedle device 106, the dose timer 234 initially displays the length of time that the microneedle device 106 is to be worn by the patient prior to removal. The timer 234 then counts down to zero in order to instruct the patient or caregiver to remove the microneedle device 106 from the skin for disposal. For example, as shown in FIG. 10A, the dose timer 234 is indicating that the microneedle device 106 should be worn for 12 additional minutes.

Figure 11:
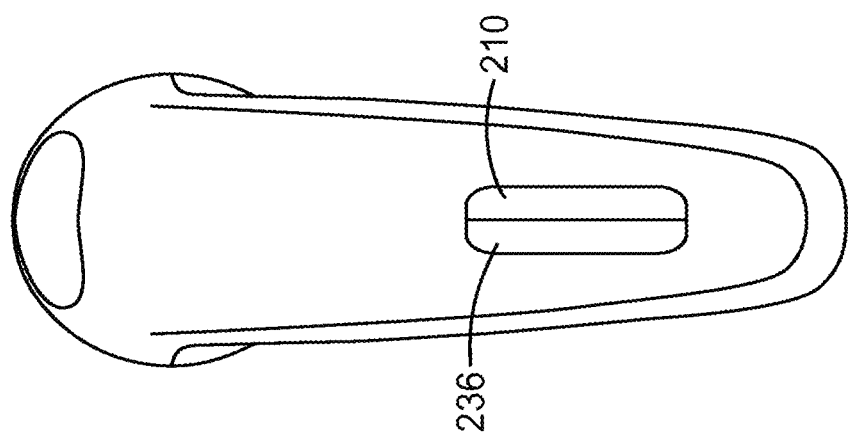
FIG. 11 is a side elevation view a device life indicator and dose timer countdown feature according to one embodiment of the present disclosure.

In one embodiment, as shown in FIG. 11, the dose timer 236 takes the form of a light bar which can indicate one color, such as orange, to instruct the user that the microneedle device 106 is still being worn and a second color, such as green, to instruct the user to remove the microneedle device 106.

Although the device life indicator 210 and dose timer 234 are described above with respect to visual representations, it should be understood that these can be replaced by or augmented with audible feedback. For example, the device can say "READY" to indicate the ready-to-fire state or it can count down the number of minutes remaining and say "Remove microneedle" when the dose timer 234 reaches zero.

Once the device 200 has been powered on 240 and undergone the device check 250, the user may then perform the priming step 270, which is described in more detail above. The device 200 then performs an internal step of incrementing the cycle count 280 and awaits actuation. If the device has not been actuated within a predetermined time, such as 2 minutes, then the device will beep intermittently 282 to alert the user that it is primed and ready to use. In one embodiment, if the device has still not been actuated within a second predetermined time period, such as 30 minutes, then the device will automatically power off 284.

As described in more detail above, the user performs the step 290 of placing the device on a skin surface and presses down on the device to partially retract the alignment arms 412A,B,C,D. The device performs an internal checking step 292 to determine if the device is aligned. If the device is not aligned, then the device is in a state 294 where the actuation button 430 will not depress and actuate the device. If the device is aligned, then the user may perform the step 296 of pressing the actuation button 430 which actuates the device and applies the microneedle device 106 to the skin. The dose timer 234, if included, begins counting down 298 (or optionally counting up) to indicate the proper dosing period. When the dose timer 234 has counted down to zero (or optionally counted up to the full dosing time) it performs an alerting step 299 to inform the user to remove the microneedle device 106 from the skin. The device subsequently powers off 284 and returns to an idle state.

In discussing the applicators of the present disclosure, the term "downward," and variations thereof, is sometimes used to describe the direction in which microneedles are pressed into skin, and "upward" to describe the opposite direction. However, those of skill in the art will understand that the applicators can be used where the microneedles are pressed into skin at an angle to the direction of the earth's gravity, or even in a direction contrary to that of the earth's gravity, and these terms are only used for simplicity and clarity to describe relative directions.

The term "transdermally," and variations thereof, is generally used to refer to any type of delivery of an active ingredient that crosses any portion of skin. That is, transdermally can generally include systemic delivery (i.e., where the active ingredient is transported across, or substantially through, the dermis such that the active ingredient is delivered into the bloodstream), as well as intradermal delivery (i.e., where the active ingredient is transported partially through the dermis, e.g., across the outer layer (stratum corneum) of the skin, where the active ingredient is delivered into the skin, e.g., for treating psoriasis or for local anesthetic delivery). That is, transdermal delivery as used herein includes delivery of an active ingredient that is transported across at least a portion of skin (but not necessarily all of the layers of skin), rather than merely being topically applied to an outer layer of the skin.

The "microneedle device" 106 can also be referred to as a "microneedle array assembly" and can include the array 107 of microneedles 108 (or, collectively, the "microneedle array" 107) and any supporting structure or substrate used to support the microneedle array 107 and/or to couple the microneedle array 107 to other structures or components of the applicator 100.

As mentioned above, in some embodiments, active ingredients or agents (e.g., drugs) can be delivered via the microneedles 108 (e.g., via solid or hollow microneedles, as described below). Examples of pharmaceutically active agents (also referred to as "drugs") that can be incorporated into the applicators of the present disclosure are those capable of local or systemic effect when administered to the skin. Some examples include buprenorphine, clonidine, diclofenac, estradiol, granisetron, isosorbide dinitrate, levonorgestrel, lidocaine, methylphenidate, nicotine, nitroglycerine, oxybutynin, rivastigmine, rotigotine, scopolamine, selegiline, testosterone, tulobuterol, and fentanyl, which are commercially available in the form of transdermal devices. Other examples include antiinflammatory drugs, both steroidal (e.g., hydrocortisone, prednisolone, triamcinolone) and nonsteroidal (e.g., naproxen, piroxicam); bacteriostatic agents (e.g., chlorhexidine, hexylresorcinol); antibacterials (e.g., penicillins such as penicillin V, cephalosporins such as cephalexin, erythromycin, tetracycline, gentamycin, sulfathiazole, nitrofurantoin, and quinolones such as norfloxacin, flumequine, and ibafloxacin); antiprotazoals (e.g., metronidazole); antifungals (e.g., nystatin); coronary vasodilators; calcium channel blockers (e.g., nifedipine, diltiazem); bronchodilators (e.g., theophylline, pirbuterol, salmeterol, isoproterenol); enzyme inhibitors such as collagenase inhibitors, protease inhibitors, acetylcholinesterase inhibitors (e.g., donepezil), elastase inhibitors, lipoxygenase inhibitors (e.g., A64077), and angiotensin converting enzyme inhibitors (e.g., captopril, lisinopril); other antihypertensives (e.g., propranolol); leukotriene antagonists (e.g., ICI204,219); anti-ulceratives such as H2 antagonists; steroidal hormones (e.g., progesterone); antivirals and/or immunomodulators (e.g., 1-isobutyl-1H-imidazo[4,5-c]quinolin-4-amine, 1-(2-hydroxy-2-methylpropyl)-1H-imidazo[4,5-c]quinolin-4-amine, N-[4-(4-amino-2-ethyl-1H-imidazo[4,5-c]quinolin-1-yl)butyl]methanesulfonamide, and acyclovir); local anesthetics (e.g., benzocaine, propofol, tetracaine, prilocaine); cardiotonics (e.g., digitalis, digoxin); antitussives (e.g., codeine, dextromethorphan); antihistamines (e.g., diphenhydramine, chlorpheniramine, terfenadine); narcotic analgesics (e.g., morphine, fentanyl citrate, sufentanil, hydromorphonc hydrochloride); peptide hormones (e.g., human or animal growth hormones, LHRH, parathyroid hormones); cardioactive products such as atriopeptides; antidiabetic agents (e.g., insulin, exanatide); enzymes (e.g., anti-plaque enzymes, lysozyme, dextranase); antinauseants; anticonvulsants (e.g., carbamazine); immunosuppressives (e.g., cyclosporine); psychotherapeutics (e.g., diazepam); sedatives (e.g., phenobarbital); anticoagulants (e.g., heparin, enoxaparin sodium); analgesics (e.g., acetaminophen); antimigraine agents (e.g., ergotamine, melatonin, sumatriptan, zolmitriptan); antiarrhythmic agents (e.g., flecainide); antiemetics (e.g., metaclopromide, ondansetron, granisetron hydrochloride); anticancer agents (e.g., methotrexate); neurologic agents such as anxiolytic drugs; hemostatics; anti-obesity agents; dopamine agonists (e.g., apomorphinc); GnRH agonists (e.g., leuprolide, goscrclin, nafarelin); fertility hormones (e.g., hCG, hMG, urofollitropin); interferons (e.g., interferon-alpha, interferon-beta, interferon-gamma, pegylated interferon-alpha); and the like, as well as pharmaceutically acceptable salts and esters thereof. The amount of drug that constitutes a therapeutically effective amount can be readily determined by those skilled in the art with due consideration of the particular drug, the particular carrier, and the desired therapeutic effect.

In some embodiments, peptide therapeutic agents (natural, synthetic, or recombinant) can be delivered via the microneedles 108 (e.g., via solid or hollow microneedles, as described below). Examples of peptide therapeutic agents that can be incorporated into the applicators of the present disclosure include parathyroid hormone (PTH), parathyroid hormone related protein (PTHrP), calcitonin, lysozyme, insulin, insulinotropic analogs, glatiramer acetate, goserelin acetate, somatostatin, octreotide, leuprolide, vasopressin, desmopressin, thymosin alpha-1, atrial natriuretic peptide (ANP), endorphin, vascular endothelial growth factor (VEGF), fibroblast-growth factor (FGF), erythropoietin (EPO), bone morphogenetic proteins (BMPs), epidermal growth factor (EFG), granulocyte colony-stimulating factor (G-CSF), granulocyte macrophage colony stimulating factor (GM-CSF), insulin-like growth factor (IGF), platelet-derived growth factor (PDGF), growth hormone release hormone (GHRH), dornase alfa, tissue plasminogen activator (tPA), urokinase, ANP clearance inhibitors, lutenizing hormone releasing hormone (LHRH), melanocyte stimulating hormones (alpha & beta MSH), pituitary hormones (hGH), adrenocorticotropic hormone (ACTH), human chorionic gonadotropin (hCG), streptokinase, interleukins (e.g. IL-2, IL-4, IL-10, IL-12, IL-15, IL-18), protein C, protein S, angiotensin, angiogenin, endothelins, pentigetide, brain natriuretic peptide (BNP), neuropeptide Y, islet amyloid polypeptide (IAPP), vasoactive intestinal peptide (VIP), hirudin, glucagon, oxytocin, and derivatives of any of the foregoing peptide therapeutic agents.

In some embodiments, drugs that are of a large molecular weight may be delivered transdermally. Increasing molecular weight of a drug typically can cause a decrease in unassisted transdermal delivery. Examples of such large molecules include proteins, peptides, nucleotide sequences, monoclonal antibodies, vaccines, polysaccharides, such as heparin, and antibiotics, such as ceftriaxone. Examples of suitable vaccines include therapeutic cancer vaccines, anthrax vaccine, flu vaccine, Lyme disease vaccine, rabies vaccine, measles vaccine, mumps vaccine, chicken pox vaccine, small pox vaccine, hepatitis vaccine, hepatitis A vaccine, hepatitis B vaccine, hepatitis C vaccine, pertussis vaccine, rubella vaccine, diphtheria vaccine, encephalitis vaccine, Japanese encephalitis vaccine, respiratory syncytial virus vaccine, yellow fever vaccine, recombinant protein vaccine, DNA vaccines, polio vaccine, therapeutic cancer vaccine, herpes vaccine, human papilloma virus vaccine, pneumococcal vaccine, meningitis vaccine, whooping cough vaccine, tetanus vaccine, typhoid fever vaccine, cholera vaccine, tuberculosis vaccine, severe acute respiratory syndrome (SARS) vaccine, HSV-1 vaccine, HSV-2 vaccine, HIV vaccine and combinations thereof. The term "vaccine" thus includes, without limitation, antigens in the forms of proteins, polysaccharides, oligosaccharides, or weakened or killed viruses. Additional examples of suitable vaccines and vaccine adjuvants are described in U.S. Patent Application Publication No. 2004/0049150 (Dalton et al.), the disclosure of which is hereby incorporated by reference.

In another embodiment, small-molecule drugs that are otherwise difficult or impossible to deliver by passive transdermal delivery may be used. Examples of such molecules include salt forms; ionic molecules, such as bisphosphonates, including sodium alendronate or pamedronate; and molecules with physicochemical properties that are not conducive to passive transdermal delivery.

Microneedle arrays useful for practicing the present disclosure can have a variety of configurations and features, such as those described in the following patents and patent applications, the disclosures of which are incorporated herein by reference. One embodiment for the microneedle arrays includes the structures disclosed in U.S. Patent Application Publication No. 2005/0261631 (Clarke et al.), which describes microneedles having a truncated tapered shape and a controlled aspect ratio. Another embodiment for the microneedle arrays includes the structures disclosed in U.S. Pat. No. 6,091,975 (Daddona et al.), which describes blade-like microprotrusions for piercing the skin. Still another embodiment for the microneedle arrays includes the structures disclosed in U.S. Pat. No. 6,312,612 (Sherman et al.), which describes tapered structures having a hollow central channel. Yet still another embodiment for the microneedle arrays includes the structures disclosed in U.S. Pat. No. 6,379,324 (Gartstein et al.), which describes hollow microneedles having at least one longitudinal blade at the top surface of the tip of the microneedle. A further embodiment for the microneedle arrays includes the structures disclosed in U.S. Patent Application Publication Nos. US2012/0123387(Gonzalez et al.) and US2011/0213335 (Burton et al.), which both describe hollow microneedles. A still further embodiment for the microneedle arrays includes the structures disclosed in U.S. Pat. No. 6,558,361 (Yeshurun) and U.S. Pat. No. 7,648,484 (Yeshurun et al.), which both describe hollow microneedle arrays and methods of manufacturing thereof.

Various embodiments of microneedles that can be employed in the microneedle arrays of the present disclosure are described in PCT Publication No. WO2012/074576 (Duan et al.), which describes liquid crystalline polymer (LCP) microneedles; and PCT Publication No. WO2012/122162 (Zhang et al.), which describes a variety of different types and compositions of microneedles that can be employed in the microneedles of the present disclosure.

In some embodiments, the microneedle material can be (or include) silicon, glass, or a metal such as stainless steel, titanium, or nickel titanium alloy. In some embodiments, the microneedle material can be (or include) a polymeric material, preferably a medical grade polymeric material. Exemplary types of medical grade polymeric materials include polycarbonate, liquid crystalline polymer (LCP), polyether ether ketone (PEEK), cyclic olefin copolymer (COC), polybutylene terephthalate (PBT). Preferred types of medical grade polymeric materials include polycarbonate and LCP.

In some embodiments, the microneedle material can be (or include) a biodegradable polymeric material, preferably a medical grade biodegradable polymeric material. Exemplary types of medical grade biodegradable materials include polylactic acid (PLA), polyglycolic acid (PGA), PGA and PLA copolymer, polyester-amide polymer (PEA).

In some embodiments, the microneedles can be a prepared from a dissolvable, degradable, or disintegradable material referred to herein as "dissolvable microneedles". A dissolvable, degradable, or disintegradable material is any solid material that dissolves, degrades, or disintegrates during use. In particular, a "dissolvable microneedle" dissolves, degrades, or disintegrates sufficiently in the tissue underlying the stratum corneum to allow a therapeutic agent to be released into the tissue. The therapeutic agent may be coated on or incorporated into a dissolvable microneedle. In some embodiments, the dissolvable material is selected from a carbohydrate or a sugar. In some embodiments, the dissolvable material is polyvinyl pyrrolidone (PVP). In some embodiments, the dissolvable material is selected from the group consisting of hyaluronic acid, carboxymethylcellulose, hydroxypropylmethylcellulose, methylcellulose, polyvinyl alcohol, sucrose, glucose, dextran, trehalose, maltodextrin, and a combination thereof.

In some embodiments, the microneedles can be made from (or include) a combination of two or more of any of the above mentioned materials. For example, the tip of a microneedle may be a dissolvable material, while the remainder of the microneedle is a medical grade polymeric material.

A microneedle or the plurality of microneedles in a microneedle array useful for practicing the present disclosure can have a variety of shapes that are capable of piercing the stratum corneum. In some embodiments, one or more of the plurality of microneedles can have a square pyramidal shape, triangular pyramidal shape, stepped pyramidal shape, conical shape, microblade shape, or the shape of a hypodermic needle. In some embodiments, one or more of the plurality of microneedles can have a square pyramidal shape. In some embodiments, one or more of the plurality of microneedles can have a triangular pyramidal shape. In some embodiments, one or more of the plurality of microneedles can have a stepped pyramidal shape. In some embodiments, one or more of the plurality of microneedles can have a conical shape. In some embodiments, one or more of the plurality of microneedles can have a microblade shape. In some embodiments, one or more of the plurality of microneedles can have the shape of a hypodermic needle. The shape can be symmetric or asymmetric. The shape can be truncated (for example, the plurality of microneedles can have a truncated pyramid shape or truncated cone shape). In a preferred embodiment, the plurality of microneedles in a microneedle array each have a square pyramidal shape.

In some embodiments, the plurality of microneedles in a microneedle array are solid microneedles (that is, the microneedles are solid throughout). In some embodiments, the plurality of solid microneedles in a solid microneedle array can have a square pyramidal shape, triangular pyramidal shape, stepped pyramidal shape, conical shape, or microblade shape. In a preferred embodiment, the plurality of solid microneedles in a solid microneedle array each have a square pyramidal shape.

In some embodiments, the plurality of microneedles in a microneedle array are hollow microneedles (that is, the microneedles contain a hollow bore through the microneedle). The hollow bore can be from the base of the microneedle to the tip of the microneedle or the bore can be from the base of the microneedle to a position offset from the tip of the microneedle. In some embodiments, one or more of the plurality of hollow microneedles in a hollow microneedle array can have a conical shape, cylindrical shape, square pyramidal shape, triangular pyramidal shape, or the shape of a hypodermic needle.

In some embodiments, one or more of the plurality of hollow microneedles in a hollow microneedle array can have a conical shape. In some embodiments, one or more of the plurality of hollow microneedles in a hollow microneedle array can have a cylindrical shape. In some embodiments, one or more of the plurality of hollow microneedles in a hollow microneedle array can have a square pyramidal shape. In some embodiments, one or more of the plurality of hollow microneedles in a hollow microneedle array can have a triangular pyramidal shape. In some embodiments, one or more of the plurality of hollow microneedles in a hollow microneedle array can have the shape of a hypodermic needle. In a preferred embodiment, the plurality of hollow microneedles in a hollow microneedle array each have the shape of a conventional hypodermic needle.

Figure 7:
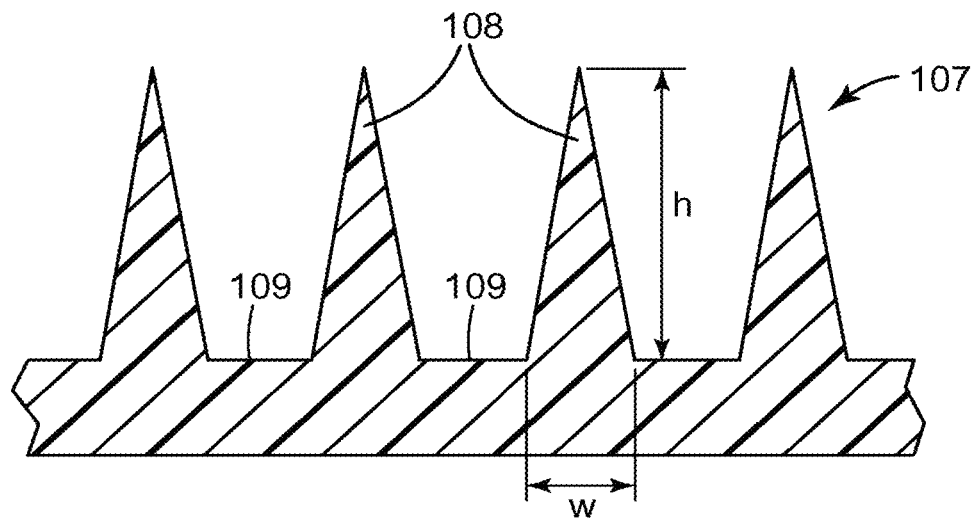
FIG. 7 is a close-up side elevational view of a microneedle array (shown with the microneedles pointing upwardly).

FIG. 7 shows a portion of the microneedle array 107 that includes four microneedles 108 (of which two are referenced in FIG. 7) positioned on a microneedle substrate 109. Each microneedle 108 has a height h, which is the length from the tip of the microneedle 108 to the microneedle base at substrate 109. Either the height of a single microneedle or the average height of all microneedles on the microneedle array can be referred to as the height of the microneedle, h.

In some embodiments, each of the plurality of microneedles (or the average of all of the plurality of microneedles) has a height of about 100 to about 3000 micrometers, in some embodiments, about 100 to about 1500 micrometers, in some embodiments, about 100 to about 1200 micrometers, and, in some embodiments, about 100 to about 1000 micrometers.

In some embodiments, each of the plurality of microneedles (or the average of all of the plurality of microneedles) has a height of about 200 to about 1200 micrometers, about 200 to about 1000 micrometers, about 200 to about 750 micrometers, or about 200 to about 600 micrometers.

In some embodiments, each of the plurality of microneedles (or the average of all of the plurality of microneedles) has a height of about 250 to about 1500 micrometers, about 500 to about 1000 micrometers, or about 500 to about 750 micrometers.

In some embodiments, each of the plurality of microneedles (or the average of all of the plurality of microneedles) has a height of about 800 to about 1400 micrometers.

In some embodiments, each of the plurality of microneedles (or the average of all of the plurality of microneedles) has a height of about 500.

In some embodiments, each of the plurality of microneedles (or the average of all of the plurality of microneedles) has a height of less than about 3000 micrometers. In other embodiments, each of the plurality of microneedles (or the average of all of the plurality of microneedles) has a height of less than about 1500 micrometers. In still other embodiments, each of the plurality of microneedles (or the average of all of the plurality of microneedles) has a height of less than about 1200 micrometers. In yet still other embodiments, each of the plurality of microneedles (or the average of all of the plurality of microneedles) has a height of less than about 1000 micrometers. In further embodiments, each of the plurality of microneedles (or the average of all of the plurality of microneedles) has a height of less than about 750 micrometers. In still further embodiments, each of the plurality of microneedles (or the average of all of the plurality of microneedles) has a height of less than about 600 micrometers.

In some embodiments, each of the plurality of microneedles (or the average of all of the plurality of microneedles) has a height of at least about 100 micrometers. In other embodiments, each of the plurality of microneedles (or the average of all of the plurality of microneedles) has a height of at least about 200 micrometers. In still other embodiments, each of the plurality of microneedles (or the average of all of the plurality of microneedles) has a height of at least about 250 micrometers. In further embodiments, each of the plurality of microneedles (or the average of all of the plurality of microneedles) has a height of at least about 500 micrometers. In still further embodiments, each of the plurality of microneedles (or the average of all of the plurality of microneedles) has a height of at least about 800 micrometers.

In some embodiments employing solid microneedles, each of the plurality of solid microneedles (or the average of all of the plurality of solid microneedles) has a height of about 100 to about 1500 micrometers, about 100 to about 1200 micrometers, about 200 to about 1000 micrometers, about 200 to about 750 micrometers, about 200 to about 600 micrometers, or about 500 micrometers.

In some embodiments employing hollow microneedles, each of the plurality of hollow microneedles (or the average of all of the plurality of hollow microneedles) has a height of about 100 to about 3000 micrometers, about 800 to about 1400 micrometers, or about 500 micrometers.

In some embodiments, each of the plurality of hollow microneedles (or the average of all of the plurality of hollow microneedles) has a height of about 900 to about 1000 micrometers. In other embodiments, each of the plurality of hollow microneedles (or the average of all of the plurality of hollow microneedles) has a height of about 900 to about 950 micrometers. In still other embodiments, each of the plurality of hollow microneedles (or the average of all of the plurality of hollow microneedles) has a height of about 900 micrometers.

A single microneedle or the plurality of microneedles in a microneedle array can also be characterized by their aspect ratio. The aspect ratio of a microneedle is the ratio of the height of the microneedle, h to the width (at the base of the microneedle), w (as shown in FIG. 7). The aspect ratio can be presented as h:w. In some embodiments, each of the plurality of microneedles (or the average of all the plurality of microneedles) has (have) an aspect ratio in the range of 2:1 to 5:1. In some of these embodiments, each of the plurality of microneedles (or the average of all of the plurality of microneedles) has (have) an aspect ratio of at least 3:1.

In some embodiments, the array of microneedles contains about 100 to about 1500 microneedles per $cm^2$ of the array of microneedles.

In some embodiments employing solid microneedles, the array of solid microneedles contains about 100 to about 1500 solid microneedles per $cm^2$ of the array of solid microneedles.

In some embodiments, the array of solid microneedles contains about 200 to about 500 solid microneedles per $cm^2$ of the array of solid microneedles.

In some embodiments, the array of solid microneedles contains about 300 to about 400 solid microneedles per $cm^2$ of the array of solid microneedles.

In some embodiments employing hollow microneedles, the array of hollow microneedles contains about 3 to about 30 hollow microneedles per array of hollow microneedles.

In some embodiments, the array of hollow microneedles contains about 10 to about 30 hollow microneedles per array of hollow microneedles.

In some embodiments, the array of hollow microneedles contains about 3 to about 20 hollow microneedles per array of hollow microneedles.

In some embodiments, the array of hollow microneedles contains about 13 to about 20 hollow microneedles per array of hollow microneedles.

In some embodiments, the array of hollow microneedles contains about 8 to about 18 hollow microneedles per array of hollow microneedles.

In some embodiments, the array of hollow microneedles contains about 18 hollow microneedles per array of hollow microneedles.

In some embodiments, the array of hollow microneedles contains about 12 hollow microneedles per array of hollow microneedles.

In some embodiments, each of the plurality of microneedles (or the average of all of the plurality of microneedles) in a microneedle array can penetrate into the skin to a depth of about 50 to about 1500 micrometers, about 50 to about 400 micrometers, or about 50 to about 250 micrometers.

In some embodiments, each of the plurality of microneedles (or the average of all of the plurality of microneedles) in a microneedle array can penetrate into the skin to a depth of about 100 to about 400 micrometers, or about 100 to about 300 micrometers.

In some embodiments, each of the plurality of microneedles (or the average of all of the plurality of microneedles) in a microneedle array can penetrate into the skin to a depth of about 150 to about 1500 micrometers, or about 800 to about 1500 micrometers.

In some embodiments, each of the plurality of microneedles (or the average of all of the plurality of microneedles) in a microneedle array can penetrate into the skin to a depth of about 400 to about 800 micrometers.

For all of the above embodiments, it will be appreciated that the depth of penetration (DOP) of each of the plurality of microneedles (or the average of all of the plurality of microneedles) in a microneedle array may not be the full length of the microneedles themselves.

Figure 8:
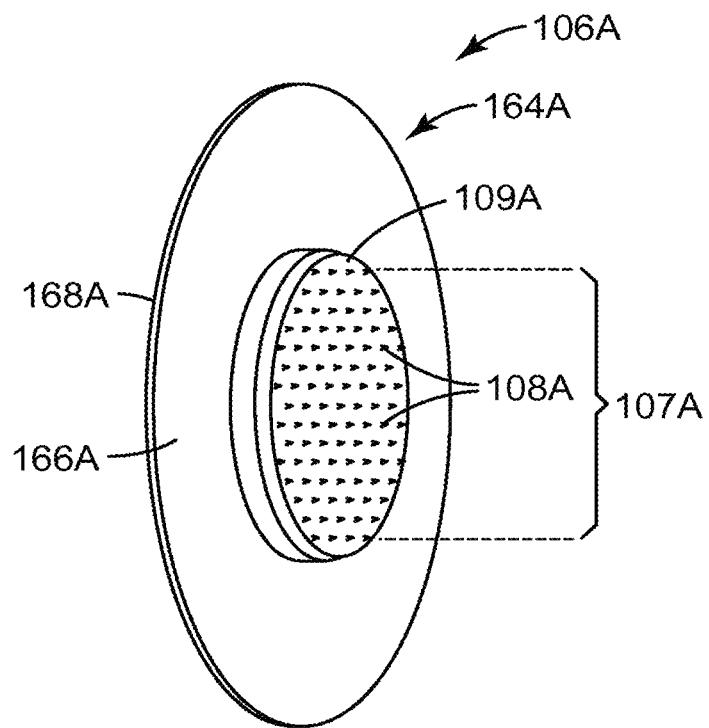
FIG. 8 is a perspective view of a microneedle device according to one embodiment of the present disclosure.

In some embodiments, the microneedle device according to the present disclosure can be in the form of a patch. One example of such an embodiment is shown in more detail in FIG. 8. FIG. 8 illustrates a microneedle device 106A comprising a patch 164A in the form of a combination of a microneedle array 107A, pressure sensitive adhesive 166A, and backing 168A. The microneedle array 107A is illustrated with microneedles 108A protruding from a microneedle substrate 109A. The microneedles 108A can be arranged in any desired pattern or distributed over the microneedle substrate 109A randomly. As shown, the microneedles 108A are arranged in uniformly spaced rows. When arranged in rows, the rows can be arranged so that the microneedles 108A are aligned or offset. In some embodiments (not shown), the microneedles 108A can be arranged in a polygonal pattern such as a triangle, square, rectangle, pentagon, hexagon, heptagon, octagon, or trapezoid. In other embodiments (not shown), the microneedles 108A can be arranged in a circular or oval pattern.

It should be understood that any description herein with respect to the microneedle device 106, the microneedle array 107, the microneedles 108, and the microneedle substrate 109 can equally apply to the microneedle device 106A, the microneedle array 107A, the microneedles 108A, and the microneedle substrate 109A, respectively, and vice versa.

In some embodiments, the surface area of the substrate 109, 109A covered with microneedles 108, 108A is about 0.1 $cm^2$ to about 20 $cm^2$. In some of these embodiments, the surface area of the substrate 109, 109A covered with microneedles 108, 108A is about 0.5 $cm^2$ to about 5 $cm^2$. In some other of these embodiments, the surface area of the substrate 109, 109A covered with microneedles 108, 108A is about 1 $cm^2$ to about 3 $cm^2$. In still other of these embodiments, the surface area of the substrate 109, 109A covered with microneedles 108, 108A is about 1 cm² to about 2 cm².

In some embodiments (e.g., as shown in FIG. 8), the microneedles of the present disclosure can be disposed over substantially the entire surface of the array. In other embodiments (not shown), a portion of the substrate may not be provided with microneedles (that is, a portion of the substrate is non-structured). In some of these embodiments, the non-structured surface has an area of more than about 1 percent and less than about 75 percent of the total area of the device surface that faces the skin surface. In another of these embodiments, the non-structured surface has an area of more than about 0.65 cm² (0.10 square inch) to less than about 6.5 cm² (1 square inch).

For hollow microneedles, a hollow channel or bore extends through the substrate 109, 109A and microneedles 108, 108A. In some embodiments, the bore exits at a channel opening at or near the tip of the hollow microneedle. The channel preferably exits at an opening near the tip of the hollow microneedle. Most preferably, the channel or bore continues along a central axis of the microneedle, but exits similar to a hypodermic needle on a sloping side-wall of the microneedle to help prevent blockage of the channel by tissue upon insertion. In some embodiments, the diameter of the channel bore is about 10 to about 200 micrometers. In other embodiments, the diameter of the channel bore is about 10 to about 150 micrometers. In still other embodiments, the diameter of the channel bore is about 30 to about 60 micrometers.

In some embodiments of hollow microneedles, the average cross-sectional area of the channel bore is about 75 to about 32,000 micrometers. In other embodiments of hollow microneedles, the average cross-sectional area of the channel bore is about 75 to about 18,000 micrometers. In still other embodiments of hollow microneedles, the average cross-sectional area of the channel bore is about 700 to about 3,000 micrometers.

In some embodiments of hollow microneedle arrays, the average spacing between adjacent microneedles (as measured from microneedle tip to microneedle tip) is between about 0.7 mm and about 20 mm. In other embodiments of hollow microneedle arrays, the average spacing between adjacent microneedles is between about 0.7 mm and about 10 mm. In still other embodiments of hollow microneedle arrays, the average spacing between adjacent microneedles is between about 2 mm and about 20 mm. In still other embodiments of hollow microneedle arrays, the average spacing between adjacent microneedles is between about 2 mm and about 10 mm. In a preferred embodiment of hollow microneedle arrays, the average spacing between adjacent microneedles is between about 2 mm.

In some embodiments of hollow microneedle arrays, the average spacing between adjacent microneedles (as measured from microneedle tip to microneedle tip) is greater than about 0.7 mm. In other embodiments of hollow microneedle arrays, the average spacing between adjacent microneedles is greater than about 2 mm.

In some embodiments of hollow microneedle arrays, the average spacing between adjacent microneedles is less than about 20 mm. In other embodiments of hollow microneedle arrays, the average spacing between adjacent microneedles is less than about 10 mm.

In some embodiments of solid microneedle arrays, the average spacing between adjacent microneedles (as measured from microneedle tip to microneedle tip) is between about 200 micrometers and about 2000 micrometers. In other embodiments of solid microneedle arrays, the average spacing between adjacent microneedles is between about 200 micrometers and about 600 micrometers. In still other embodiments of solid microneedle arrays, the average spacing between adjacent microneedles is between about 200 micrometers and about 300 micrometers. In yet still other embodiments of solid microneedle arrays, the average spacing between adjacent microneedles is between about 500 micrometers and about 600 micrometers.

In some embodiments of solid microneedle arrays, the average spacing between adjacent microneedles (as measured from microneedle tip to microneedle tip) is greater than about 200 micrometers. In other embodiments of solid microneedle arrays, the average spacing between adjacent microneedles is greater than about 500 micrometers.

In some embodiments of solid microneedle arrays, the average spacing between adjacent microneedles is less than about 2000 micrometers. In other embodiments of solid microneedle arrays, the average spacing between adjacent microneedles is less than about 1000 micrometers. In still other embodiments of solid microneedle arrays, the average spacing between adjacent microneedles is less than about 600 micrometers. In yet still other embodiments of solid microneedle arrays, the average spacing between adjacent microneedles is less than about 300 micrometers.

The microneedle arrays can be manufactured in any suitable way such as by injection molding, compression molding, metal injection molding, stamping, photolithography, or extrusion. In one embodiment, hollow microneedle arrays can be made by injection molding of a polymer such as medical grade polycarbonate or LCP, followed by laser drilling to form the channels of the microneedles.

Each embodiment shown in the figures is illustrated as a separate embodiment for clarity in illustrating a variety of features of the applicators of the present disclosure. However, it should be understood that any combination of elements and features of any of the embodiments illustrated in the figures and described herein can be employed in the applicators of the present disclosure.

The following embodiments are intended to be illustrative of the present disclosure and not limiting.

Embodiments

Embodiment 1 is an applicator for applying a microneedle device, comprising:
  a housing having a first open end configured so as to accept the microneedle device,
  a second end configured as a graspable handle,
  a driving element contained within the housing, the driving element having a first end configured so as to couple with the microneedle device,
  an actuation button in mechanical or electrical engagement with the driving element,
  at least one reciprocating support structure slidably engaged with the housing, wherein the reciprocating support structure has a first position where at least a portion of it extends from the first open end of the housing by a first distance and a second position wherein the portion extends from the first open end of the housing by a second distance, the second distance being less than the first distance.

Embodiment 2 is the applicator of embodiment 1 wherein the reciprocating support structure comprises a plurality of alignment feet Embodiment 3 is the applicator of embodiment 2 wherein the alignment feet are independently movable.

Embodiment 4 is the applicator of embodiment 2 or 3 and further comprising a lockout mechanism that prevents actuation if the alignment feet are not evenly aligned.

Embodiment 5 is the applicator of any of the preceding embodiments wherein the portion of the reciprocating support structure that extends from the first open end of the housing has an open, cylindrical end.

Embodiment 6 is the applicator of any of the preceding embodiments wherein the driving element comprises a magnet.

Embodiment 7 is the applicator of any of the preceding embodiments wherein the applicator further comprises a dose timer in mechanical or electrical engagement with at least one of the driving element or the actuation button, wherein the dose timer is capable of determining the time that has elapsed after actuation of the device and providing feedback to the user as to the time that the microneedle device has been in place on the skin surface.

Embodiment 8 is the applicator of any one of the preceding embodiments wherein the applicator further comprises a driving spring coupled to the driving element.

Embodiment 9 is the applicator of any of the preceding embodiments wherein the applicator further comprises a device life indicator in mechanical or electrical engagement with at least one of the driving element or the actuation button, wherein the device life indicator is capable of counting the number of use cycles that the applicator has undergone and, based on the number of use cycles, providing feedback to the user as to the use status of the applicator.

Embodiment 10 is an applicator for applying a microneedle device, comprising:
 a housing having a first open end configured so as to accept the microneedle device,
 a second end configured as a graspable handle,
 a driving element contained within the housing, the driving element having a first end configured so as to couple with the microneedle device,
 a microneedle device,
 an actuation button in mechanical or electrical engagement with the driving element,
 a device life indicator in mechanical or electrical engagement with at least one of the driving element or the actuation button, wherein the device life indicator is capable of counting the number of use cycles that the applicator has undergone and, based on the number of use cycles, providing feedback to the user as to the use status of the applicator.

Embodiment 11 is the applicator of embodiment 9 or 10 wherein the device life indicator is a dose counter.

Embodiment 12 is the applicator of any of embodiments 9 to 11 wherein the device includes a lockout mechanism that prevents device actuation when the device life indicator has counted a predetermined number of use cycles.

Embodiment 13 is the applicator of any of embodiments 9 to 12 wherein the device life indicator comprises a numeric display.

Embodiment 14 is the applicator of any of embodiments 9 to 13 wherein the device life indicator comprises a colored graphic display that can change in response to changes in device status.

Embodiment 15 is the applicator of any of embodiments 9 to 14 wherein the device life indicator comprises one or more words that are visually displayed.

Embodiment 16 is the applicator of any of embodiments 9 to 15 wherein the applicator further comprises a dose timer in mechanical or electrical engagement with at least one of the driving element or the actuation button, wherein the dose timer is capable of determining the time that has elapsed after actuation of the device and providing feedback to the user as to the time that the microneedle device has been in place on the skin surface.

Embodiment 17 is the applicator of any one of the preceding embodiments wherein the device includes a device status indicator, wherein the device status indicator is optionally capable of displaying a message in response to the device being in a specific state.

Embodiment 18 is an applicator for applying a microneedle device, comprising:
 a housing having a first open end configured so as to accept the microneedle device,
 a second end configured as a graspable handle,
 a driving element contained within the housing, the driving element having a first end configured so as to couple with the microneedle device,
 an actuation button in mechanical or electrical engagement with the driving element,
 wherein the driving element is configured to apply the microneedle device to a skin surface when the actuation button is actuated,
 wherein the microneedle device is releasably coupled to the driving element, and
 a dose timer in mechanical or electrical engagement with at least one of the driving element or the actuation button, wherein the dose timer is capable of determining the time that has elapsed after actuation of the device and providing feedback to the user as to the time that the microneedle device has been in place on the skin surface.

Embodiment 19 is the applicator of any one of the preceding embodiments wherein the applicator further comprises a battery.

Embodiment 20 is the applicator of embodiment 19 wherein the applicator further comprises a battery gauge to indicate the amount of usable battery life remaining.

The embodiments described above and illustrated in the figures are presented by way of example only and are not intended as a limitation upon the concepts and principles of the present disclosure. As such, it will be appreciated by one having ordinary skill in the art that various changes in the elements and their configuration and arrangement are possible without departing from the spirit and scope of the present disclosure.

All references and publications cited herein are expressly incorporated herein by reference in their entirety into this disclosure.

Various features and aspects of the present disclosure are set forth in the following claims.

What is claimed is:

1. An applicator for applying a microneedle device, the applicator comprising:
 the microneedle device;
 a housing having a first open end configured so as to accept the microneedle device and a second end of the housing configured as a graspable handle;
 a driving element contained within the housing, the driving element having a first end configured so as to couple with the microneedle device;
 an actuation button in mechanical or electrical engagement with the driving element;
 a device life indicator in mechanical or electrical engagement with at least one of the driving element or the actuation button, wherein the device life indicator is capable of counting a number of use cycles that the applicator has undergone and, based on the number of use cycles, providing feedback to a user as to a use status of the applicator; and
a lockout mechanism configured to unlock the driving element if the number of use cycles meets predetermined acceptance criteria.

2. The applicator of claim 1, wherein the device life indicator is a dose counter.

3. The applicator of claim 1, wherein the lockout mechanism prevents actuation of the applicator when the device life indicator has counted a predetermined number of use cycles.

4. The applicator of claim 1, wherein the device life indicator comprises a numeric display.

5. The applicator of claim 1, wherein the device life indicator comprises a colored graphic display that can change in response to changes in the use status of the applicator.

6. The applicator of claim 1, wherein the device life indicator comprises one or more words that are visually displayed.

7. The applicator of claim 1, wherein the applicator further comprises a dose timer in mechanical or electrical engagement with at least one of the driving element or the actuation button, wherein the dose timer is capable of determining a time that has elapsed after actuation of the applicator and providing feedback to the user as to a time that the microneedle device has been in place on a surface of skin.

8. The applicator of claim 1, wherein the applicator includes a device status indicator, wherein the device status indicator is capable of displaying a message in response to the applicator being in a specific state.

9. The applicator of claim 1, further comprising a reciprocating support structure slidably engaged with the housing, wherein the reciprocating support structure has a first position where at least a portion of the reciprocating support structure extends from the first open end of the housing by a first distance and a second position wherein the portion of the reciprocating support structure extends from the first open end of the housing by a second distance, the second distance being less than the first distance.

10. The applicator of claim 9, wherein the reciprocating support structure comprises a plurality of alignment feet.

11. The applicator of claim 10, wherein each of the plurality of alignment feet is independently movable.

12. The applicator of claim 10, wherein the lockout mechanism prevents actuation if the plurality of alignment feet is not evenly aligned.

13. The applicator of claim 9, wherein the portion of the reciprocating support structure that extends from the first open end of the housing has an open, cylindrical end.

14. The applicator of claim 1, wherein the driving element comprises a magnet.

15. The applicator of claim 1, wherein the applicator further comprises a driving spring coupled to the driving element.

16. The applicator of claim 1, wherein the device life indicator is curved shape.

17. The applicator of claim 16, wherein the device life indicator is U-shaped.

18. The applicator of claim 1, wherein the device life indicator comprises audible feedback.

19. An applicator for applying a microneedle device, the applicator comprising:
the microneedle device;
a housing having a first open end configured so as to accept the microneedle device and a second end of the housing configured as a graspable handle;
a driving element contained within the housing, the driving element having a first end configured so as to couple with the microneedle device;
an actuation button in mechanical or electrical engagement with the driving element; and
a device life indicator in mechanical or electrical engagement with at least one of the driving element or the actuation button, wherein the device life indicator is capable of counting a number of use cycles that the applicator has undergone and, based on the number of use cycles, providing feedback to a user as to a use status of the applicator; and
a lockout mechanism configured to unlock the driving element if the number of use cycles meets predetermined acceptance criteria;
wherein the applicator is configured to:
check a cycle count from the device life indicator of the number of use cycles that the applicator has undergone;
check a battery life of the applicator;
direct the device life indicator to provide feedback to the user of a ready use status of the applicator if the cycle count and the battery life meet predetermined criteria; and
unlock the lockout mechanism if the cycle count and the battery life meet the predetermined criteria.

20. The applicator of claim 19, wherein the applicator is further configured to direct the device life indicator to provide feedback to the user of an inoperable use status of the applicator if the cycle count and the battery life do not meet the predetermined criteria.

21. The applicator of claim 19, wherein the applicator further comprises a battery gauge configured to indicate an amount of usable battery life remaining.

* * * * *